US012702665B2

(12) United States Patent
Pommier et al.

(10) Patent No.: US 12,702,665 B2
(45) Date of Patent: Aug. 11, 2026

(54) ExoVII INHIBITOR AND QUINOLONE ANTIBIOTIC COMBINATION USEFUL FOR TREATING BACTERIAL INFECTION

(71) Applicant: The United States of America, As Represented by the Secretary, Department of Health and Human Services, Bethesda, MD (US)

(72) Inventors: Yves Georges Pommier, Bethesda, MD (US); Shar-yin Naomi Huang, Bethesda, MD (US)

(73) Assignee: The United States of America, As Represented by the Secretary, Department of Health and Human Services, Bethesda, MD (US)

( * ) Notice: Subject to any disclaimer, the term of this patent is extended or adjusted under 35 U.S.C. 154(b) by 546 days.

(21) Appl. No.: 18/268,603

(22) PCT Filed: Dec. 22, 2021

(86) PCT No.: PCT/US2021/064996

§ 371 (c)(1),
(2) Date: Jun. 20, 2023

(87) PCT Pub. No.: WO2022/140631

PCT Pub. Date: Jun. 30, 2022

(65) Prior Publication Data

US 2024/0307369 A1 Sep. 19, 2024

Related U.S. Application Data

(60) Provisional application No. 63/129,271, filed on Dec. 22, 2020.

(51) Int. Cl.
*A61K 31/472* (2006.01)
*A61K 45/06* (2006.01)
*A61P 31/04* (2006.01)

(52) U.S. Cl.
CPC ............ *A61K 31/472* (2013.01); *A61K 45/06* (2013.01); *A61P 31/04* (2018.01)

(58) Field of Classification Search
CPC .............................. A61K 31/472; A61P 31/04
USPC .......................................................... 514/309
See application file for complete search history.

(56) References Cited

U.S. PATENT DOCUMENTS

2009/0264342 A1 * 10/2009 Cottarel ................. A61K 38/12 435/375

FOREIGN PATENT DOCUMENTS

WO 02/086078 A2 10/2002

OTHER PUBLICATIONS

Bradbury et al., "Recent advances in bacterial topoisomerase inhibitors", Current Opinion in Pharmacology, 2008, 8(5), 574-581.
Senaweera et al., "4-benzylideneisoquinoline-1,3(2H,4H)-diones as tyrosyl DNA phosphodiesterase 2 (TDP2) inhibitors", Medicinal Chemistry Research, 2020, 30(2), 371-386.

* cited by examiner

*Primary Examiner* — Raymond J Henley, III
(74) *Attorney, Agent, or Firm* — McDonnell Boehnen Hulbert & Berghoff LLP

(57) ABSTRACT

The disclosure provides a method of treating or preventing a bacterial infection in a subject comprising administering a therapeutically effective amount of a combination of a bacterial type IIA topoisomerase inhibitor, or a pharmaceutically acceptable salt thereof and a compound Formula I, or a pharmaceutically acceptable salt thereof, to the subject, where the compound of Formula I is (Formula (I)) where the variables, e.g. $Y^1$, $Y^2$, and $R^1$-$R^4$, are described herein. The bacterial type IIA topoisomerase inhibitor can be a quinolone antibiotic such as ciprofloxacin.

(Formula (I))

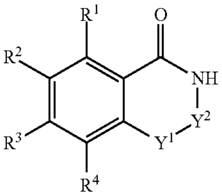

21 Claims, 19 Drawing Sheets

Specification includes a Sequence Listing.

X = Thymidine (OH-41) X = Tyrosine (Y-40)

SEQUENCE LISTING

```
<160> NUMBER OF SEQ ID NOS: 35

<210> SEQ ID NO 1
<211> LENGTH: 38
<212> TYPE: DNA
<213> ORGANISM: Artificial Sequence
<220> FEATURE:
<223> OTHER INFORMATION: gyrAHis FP

<400> SEQUENCE: 1

cggtacccgg ggatccggat gtgaataaag cgtatagg                             38


<210> SEQ ID NO 2
<211> LENGTH: 62
<212> TYPE: DNA
<213> ORGANISM: Artificial Sequence
<220> FEATURE:
<223> OTHER INFORMATION: gyrAHis BP

<400> SEQUENCE: 2

tagaatactc aagcttttag tggtgatggt gatgatgttc ttcttctggc tcgtcgtcaa     60

cg                                                                    62


<210> SEQ ID NO 3
<211> LENGTH: 21
<212> TYPE: DNA
<213> ORGANISM: Artificial Sequence
<220> FEATURE:
<223> OTHER INFORMATION: gyrA-S83L FP
```

<400> SEQUENCE: 3
catggtgact tggcggtcta t 21

<210> SEQ ID NO 4
<211> LENGTH: 21
<212> TYPE: DNA
<213> ORGANISM: Artificial Sequence
<220> FEATURE:
<223> OTHER INFORMATION: gyrA-S83L BP

<400> SEQUENCE: 4
atagaccgcc aagtcaccat g 21

<210> SEQ ID NO 5
<211> LENGTH: 60
<212> TYPE: DNA
<213> ORGANISM: Artificial Sequence
<220> FEATURE:
<223> OTHER INFORMATION: gyrA-KO-zeo-FP

<400> SEQUENCE: 5
tactccgtaa ttggcaagac aaacgagtat atcaggcatt gttgacaatt aatcatcggc 60

<210> SEQ ID NO 6
<211> LENGTH: 60
<212> TYPE: DNA
<213> ORGANISM: Artificial Sequence
<220> FEATURE:
<223> OTHER INFORMATION: gyrA-KO-zeo-BP

<400> SEQUENCE: 6
aagggagata gctccctttt ggcatgaaga agtaaaatta tcagtcctgc tcctcggcca 60

<210> SEQ ID NO 7
<211> LENGTH: 20
<212> TYPE: DNA
<213> ORGANISM: Artificial Sequence
<220> FEATURE:
<223> OTHER INFORMATION: gyrA-KO-FP

<400> SEQUENCE: 7
tcattggcac ttctactccg 20

<210> SEQ ID NO 8
<211> LENGTH: 20
<212> TYPE: DNA
<213> ORGANISM: Artificial Sequence
<220> FEATURE:
<223> OTHER INFORMATION: gyrA-KO-BP

<400> SEQUENCE: 8
aagggagata gctccctttt 20

<210> SEQ ID NO 9
<211> LENGTH: 22
<212> TYPE: DNA
<213> ORGANISM: Artificial Sequence
<220> FEATURE:
<223> OTHER INFORMATION: T-22-3PT
<220> FEATURE:
<221> NAME/KEY: misc_feature
<222> LOCATION: (19)..(22)
<223> OTHER INFORMATION: phosphorothioate bond

<400> SEQUENCE: 9
gcgcagctag cggcggatgg ca 22

<210> SEQ ID NO 10
<211> LENGTH: 18
<212> TYPE: DNA
<213> ORGANISM: Artificial Sequence
<220> FEATURE:
<223> OTHER INFORMATION: P-18
<220> FEATURE:
<221> NAME/KEY: misc_feature
<222> LOCATION: (1)..(1)
<223> OTHER INFORMATION: 5'-phosphate (P)

<400> SEQUENCE: 10
tccgttgaag cctgcttt 18

<210> SEQ ID NO 11
<211> LENGTH: 18
<212> TYPE: DNA
<213> ORGANISM: Artificial Sequence
<220> FEATURE:
<223> OTHER INFORMATION: OH-18

<400> SEQUENCE: 11
tccgttgaag cctgcttt 18

<210> SEQ ID NO 12
<211> LENGTH: 18
<212> TYPE: DNA
<213> ORGANISM: Artificial Sequence
<220> FEATURE:
<223> OTHER INFORMATION: Y-18
<220> FEATURE:
<221> NAME/KEY: misc_feature
<222> LOCATION: (1)..(1)
<223> OTHER INFORMATION: 5'-phosphotyrosine (Y)

<400> SEQUENCE: 12
tccgttgaag cctgcttt 18

<210> SEQ ID NO 13
<211> LENGTH: 19
<212> TYPE: DNA
<213> ORGANISM: Artificial Sequence
<220> FEATURE:
<223> OTHER INFORMATION: OH-19

<400> SEQUENCE: 13
ttccgttgaa gcctgcttt 19

<210> SEQ ID NO 14
<211> LENGTH: 34
<212> TYPE: DNA
<213> ORGANISM: Artificial Sequence
<220> FEATURE:
<223> OTHER INFORMATION: B-34

<400> SEQUENCE: 14
tgccatccgc cgctagctgc gcaaagcagg cttc 34

<210> SEQ ID NO 15
<211> LENGTH: 36
<212> TYPE: DNA
<213> ORGANISM: Artificial Sequence
<220> FEATURE:
<223> OTHER INFORMATION: B-36

<400> SEQUENCE: 15

-continued

```
tgccatccgc cgctagctgc gcaaagcagg cttcaa                          36


<210> SEQ ID NO 16
<211> LENGTH: 38
<212> TYPE: DNA
<213> ORGANISM: Artificial Sequence
<220> FEATURE:
<223> OTHER INFORMATION: B-38

<400> SEQUENCE: 16

tgccatccgc cgctagctgc gcaaagcagg cttcaacg                        38


<210> SEQ ID NO 17
<211> LENGTH: 40
<212> TYPE: DNA
<213> ORGANISM: Artificial Sequence
<220> FEATURE:
<223> OTHER INFORMATION: B-40

<400> SEQUENCE: 17

tgccatccgc cgctagctgc gcaaagcagg cttcaacgga                      40


<210> SEQ ID NO 18
<211> LENGTH: 15
<212> TYPE: DNA
<213> ORGANISM: Artificial Sequence
<220> FEATURE:
<223> OTHER INFORMATION: B-15

<400> SEQUENCE: 18

taaagcaggc ttcaa                                                 15


<210> SEQ ID NO 19
<211> LENGTH: 56
<212> TYPE: DNA
<213> ORGANISM: Artificial Sequence
<220> FEATURE:
<223> OTHER INFORMATION: B-56

<400> SEQUENCE: 19

tgccatccgc cgctagctgc gcactcttga ccctacgacg ataaagcagg cttcaa    56


<210> SEQ ID NO 20
<211> LENGTH: 76
<212> TYPE: DNA
<213> ORGANISM: Artificial Sequence
<220> FEATURE:
<223> OTHER INFORMATION: B-76

<400> SEQUENCE: 20

tgccatccgc cgctagctgc gcactcttga ccctacgacg atactcttga ccctacgacg    60

ataaagcagg cttcaa                                                76


<210> SEQ ID NO 21
<211> LENGTH: 20
<212> TYPE: DNA
<213> ORGANISM: Artificial Sequence
<220> FEATURE:
<223> OTHER INFORMATION: M-20
<220> FEATURE:
<221> NAME/KEY: misc_feature
<222> LOCATION: (1)..(1)
<223> OTHER INFORMATION: 5'-phosphate (P)

<400> SEQUENCE: 21
```

-continued atcgtcgtag ggtcaagagt 20

<210> SEQ ID NO 22
<211> LENGTH: 40
<212> TYPE: DNA
<213> ORGANISM: Artificial Sequence
<220> FEATURE:
<223> OTHER INFORMATION: M-40
<220> FEATURE:
<221> NAME/KEY: misc_feature
<222> LOCATION: (1)..(1)
<223> OTHER INFORMATION: 5'-phosphate (P)

<400> SEQUENCE: 22
atcgtcgtag ggtcaagagt atcgtcgtag ggtcaagagt 40

<210> SEQ ID NO 23
<211> LENGTH: 10
<212> TYPE: DNA
<213> ORGANISM: Artificial Sequence
<220> FEATURE:
<223> OTHER INFORMATION: Y-10-DNA
<220> FEATURE:
<221> NAME/KEY: misc_feature
<222> LOCATION: (1)..(1)
<223> OTHER INFORMATION: 5'-phosphotyrosine (Y)

<400> SEQUENCE: 23
ttaaaacagc 10

<210> SEQ ID NO 24
<211> LENGTH: 20
<212> TYPE: RNA
<213> ORGANISM: Artificial Sequence
<220> FEATURE:
<223> OTHER INFORMATION: Y-10-RNA
<220> FEATURE:
<221> NAME/KEY: misc_feature
<222> LOCATION: (1)..(1)
<223> OTHER INFORMATION: 5'-phosphotyrosine (Y)

<400> SEQUENCE: 24
rururarara rarcrargrc 20

<210> SEQ ID NO 25
<211> LENGTH: 28
<212> TYPE: DNA
<213> ORGANISM: Artificial Sequence
<220> FEATURE:
<223> OTHER INFORMATION: B-28

<400> SEQUENCE: 25
tgccatccgc cgctagctgc gcgctgtt 28

<210> SEQ ID NO 26
<211> LENGTH: 32
<212> TYPE: DNA
<213> ORGANISM: Artificial Sequence
<220> FEATURE:
<223> OTHER INFORMATION: B-32

<400> SEQUENCE: 26
tgccatccgc cgctagctgc gcgctgtttt aa 32

<210> SEQ ID NO 27
<211> LENGTH: 22
<212> TYPE: DNA
<213> ORGANISM: Artificial Sequence

<220> FEATURE:
<223> OTHER INFORMATION: T-22

<400> SEQUENCE: 27
gcgcagctag cggcggatgg ca 22

<210> SEQ ID NO 28
<211> LENGTH: 14
<212> TYPE: DNA
<213> ORGANISM: Artificial Sequence
<220> FEATURE:
<223> OTHER INFORMATION: 14-P
<220> FEATURE:
<221> NAME/KEY: misc_feature
<222> LOCATION: (14)..(14)
<223> OTHER INFORMATION: 3'-phosphate (P)

<400> SEQUENCE: 28
gatctaaaag actt 14

<210> SEQ ID NO 29
<211> LENGTH: 14
<212> TYPE: DNA
<213> ORGANISM: Artificial Sequence
<220> FEATURE:
<223> OTHER INFORMATION: 14-OH

<400> SEQUENCE: 29
gatctaaaag actt 14

<210> SEQ ID NO 30
<211> LENGTH: 14
<212> TYPE: DNA
<213> ORGANISM: Artificial Sequence
<220> FEATURE:
<223> OTHER INFORMATION: 14-Y
<220> FEATURE:
<221> NAME/KEY: misc_feature
<222> LOCATION: (14)..(14)
<223> OTHER INFORMATION: 3'-phosphotyrosine (Y)

<400> SEQUENCE: 30
gatctaaaag actt 14

<210> SEQ ID NO 31
<211> LENGTH: 32
<212> TYPE: DNA
<213> ORGANISM: Artificial Sequence
<220> FEATURE:
<223> OTHER INFORMATION: B32-3Y

<400> SEQUENCE: 31
cttttagatc tgccatccgc cgctagctgc gc 32

<210> SEQ ID NO 32
<211> LENGTH: 36
<212> TYPE: DNA
<213> ORGANISM: Artificial Sequence
<220> FEATURE:

-continued

```
<223> OTHER INFORMATION: B36-3Y

<400> SEQUENCE: 32

aagtctttta gatctgccat ccgccgctag ctgcgc                              36


<210> SEQ ID NO 33
<211> LENGTH: 22
<212> TYPE: DNA
<213> ORGANISM: Artificial Sequence
<220> FEATURE:
<223> OTHER INFORMATION: T-22-15PT
<220> FEATURE:
<221> NAME/KEY: misc_feature
<222> LOCATION: (7)..(22)
<223> OTHER INFORMATION: phosphorothioate bond

<400> SEQUENCE: 33

gcgcagctag cggcggatgg ca                                             22


<210> SEQ ID NO 34
<211> LENGTH: 30
<212> TYPE: DNA
<213> ORGANISM: Artificial Sequence
<220> FEATURE:
<223> OTHER INFORMATION: Gyr-1

<400> SEQUENCE: 34

gaatcataat ggggaaggcc atccagcctc                                     30


<210> SEQ ID NO 35
<211> LENGTH: 31
<212> TYPE: DNA
<213> ORGANISM: Artificial Sequence
<220> FEATURE:
<223> OTHER INFORMATION: Gyr-2

<400> SEQUENCE: 35

tgaggctgga tggccttccc cattatgatt c                                   31
```

ExoVII INHIBITOR AND QUINOLONE ANTIBIOTIC COMBINATION USEFUL FOR TREATING BACTERIAL INFECTION

CROSS REFERENCE TO RELATED APPLICATIONS

This application is the US national phase under 35 U.S.C. § 371 of International Application No. PCT/US2021/064996, filed Dec. 22, 2021, which claims priority to and the benefit of U.S. Provisional Patent Application No. 63/129,271, filed Dec. 22, 2020, the contents of each of which are hereby incorporated by reference in their entirety.

BACKGROUND

The rise of multi- and pan-resistant bacteria strains necessitates development of new classes of antibiotics. For example, mutations in type IIA topoisomerases are a well-documented mechanism for bacteria to develop resistance to quinolone antibiotics. Yet, no new classes of antibiotics have been approved by the FDA in nearly two decades.

Quinolone antibiotics, including ciprofloxacin, are on the World Health Organization's List of Essential Medicines. Collectively termed topoisomerase poisons, these drugs bind to a pocket forming transiently at the covalently linked enzyme-DNA interface during the catalytic cycles of the topoisomerases as they cleave DNA backbone(s) to modulate DNA topology. Trapping of topoisomerase-DNA covalent complexes (TOPccs) is the initiating event in the killing of bacterial and cancer cells by antibacterial and anticancer topoisomerase poisons. The repair of TOPccs in eukaryotes relies on their excision by the tyrosyl-DNA phosphodiesterase (TDP1 and TDP2) enzymes, which hydrolyze the covalent bond between the trapped topoisomerase catalytic tyrosine and the end of the broken DNA. Despite the wide use of quinolones, the repair pathways of prokaryotic topoisomerases are much less understood, and until now no TDP activity has been identified in prokaryotes.

*E. coli* strains deficient in DNA double-stranded break repair or the resolvasome machinery are hypersensitive to ciprofloxacin, as these pathways are involved in downstream repair of the TOPccs. Loss of exonuclease VII (ExoVII), a nuclease capable of degrading single-stranded DNA but without well-defined biological functions, leads to hypersensitivity to quinolones. ExoVII is well-conserved across the entire bacteria domain. In view of the finding that loss of ExoVII activity increases bacterial sensitivity to quinolones, additional studies on the role of ExoVII inhibitors in TOPcc repair were undertaken.

SUMMARY

In this disclosure we show that ExoVII inhibitors can boost the efficacy of antibiotics that inhibit prokaryotic type IIA topoisomerases, such as DNA gyrase. These antibiotics include quinolone antibiotics. ExoVII inhibitors are useful for increasing the sensitivity of antibiotic resistant bacterial strains to prokaryotic type IIA topoisomerase inhibitors. We show that ExoVII inhibitors can act as a "helper drugs," boosting the efficacy of quinolones, including in quinolone-resistant strains.

The disclosure includes a method of treating or preventing a bacterial infection in a subject comprising administering a therapeutically effective amount of a combination of a bacterial type IIA topoisomerase inhibitor and an Exo VII inhibitor, or a pharmaceutically acceptable salt of either or both of the foregoing, to the subject.

The Exo VII inhibitor can be a compound of Formula I (Formula (I))

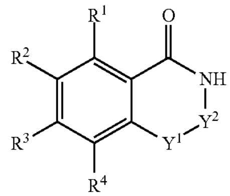

or pharmaceutically acceptable salt thereof. Within Formula I the variables, $Y^1$, $Y^2$, $R^1$, $R^2$, $R^3$, and $R^4$, carry the following definitions.

$Y^1$ is carbon substituted with oxo and $Y^2$ is $CR^6$; or $Y^1$ is $CR^5$ and $Y^2$ is carbon substituted with oxo.

$R^1$, $R^3$, and $R^4$ are independently chosen from H, halogen, hydroxyl, amino, nitro, cyano, $C_1$-$C_4$alkyl, $C_1$-$C_4$alkoxy, $C_1$-$C_2$haloalkyl, and $C_1$-$C_2$haloalkoxy.

$R^2$ is H, halogen, hydroxyl, amino, nitro, cyano, —COOH, $C_1$-$C_4$alkyl, $C_1$-$C_4$alkoxy, $C_1$-$C_2$haloalkyl, or $C_1$-$C_2$haloalkoxy; or $R^2$ is —$C_0$-$C_4$alkyl($C_3$-$C_7$cycloalkyl), —$C_0$-$C_4$alkyl(bridged $C_7$-$C_{12}$cycloalkyl), —$C_0$-$C_4$alkyl(aryl), —$C_0$-$C_4$alkyl (mono- or bi-cyclic heteroaryl), or —$C_0$-$C_4$alkyl(4- to 7-membered heterocycloalkyl), each of which is optionally substituted with one or more substituents independently chosen from $R^{10}$ and 0 or 1 substituents $R^{12}$.

$R^4$ is H, halogen, hydroxyl, amino, nitro, cyano, $C_1$-$C_4$alkyl, $C_1$-$C_4$alkoxy, $C_2$-$C_6$alkanoyl, —$C_1$-$C_6$alkylester, —$C_0$-$C_4$alkyl(mono- or di-$C_1$-$C_6$alkylamino), mono- or di-$C_1$-$C_6$alkylcarboxamide; $C_1$-$C_2$haloalkyl, or $C_1$-$C_2$haloalkoxy.

$R^5$ and $R^6$ are independently chosen from H, halogen, hydroxyl, amino, nitro, cyano, —CHO, —COOH, —$CONH_3$, $C_1$-$C_4$alkyl, $C_1$-$C_4$alkoxy, $C_1$-$C_2$haloalkyl, $C_1$-$C_2$haloalkoxy, $C_2$-$C_6$alkanoyl, $C_1$-$C_6$alkylester, —$C_0$-$C_4$alkyl(mono- and di-$C_1$-$C_6$alkylamino), and mono- and di-($C_1$-$C_6$alkyl)carboxamide.

$R^{10}$ is independently selected at each occurrence from halogen, hydroxyl, amino, nitro, cyano, —CHO, —COOH, oxo, $C_1$-$C_8$alkyl, $C_2$-$C_8$alkenyl, and $C_2$-$C_8$alkynyl, wherein in each $C_1$-$C_8$alkyl, $C_2$-$C_8$alkenyl, and $C_2$-$C_8$alkynyl, in the definition of $R^{10}$ one or more carbon atoms is optionally replaced by O, $NR^{11}$, —C(O)—, —$NR^{11}$C(O)—, —C(O)$NR^{11}$, —C(O)O—, —OC(O)—, —$S(O)_n$—, —$S(O)_nNR^{11}$, or —$NR^{11}S(O)_n$—, where n is 0, 1, or 2, and in which each $C_0$-$C_4$alkyl, $C_1$-$C_8$alkyl, $C_2$-$C_8$alkenyl, or $C_2$-$C_8$alkynyl is optionally substituted with one or more substituents $R^{13}$.

$R^{11}$ is independently chosen at each occurrence from hydrogen, $C_1$-$C_6$alkyl, and —$C_0$-$C_2$alkyl($C_3$-$C_7$cycloalkyl).

$R^{12}$ is selected from —$C_0$-$C_4$alkyl($C_3$-$C_7$cycloalkyl), —O—$C_0$-$C_4$alkyl($C_3$-$C_7$cycloalkyl), —$C_0$-$C_4$alkyl (aryl), —O—$C_0$-$C_4$alkyl(aryl), —$C_0$-$C_4$alkyl(5- to 6-membered heteroaryl), —O—$C_0$-$C_4$alkyl(5- to 6-membered heteroaryl), —$C_0$-$C_4$alkyl(3- to 6-membered heterocycloalkyl), and —O—$C_0$-$C_4$alkyl(3- to 6-membered heterocycloalkyl), each of which is optionally substituted with one or more substituents independently chosen from halogen, hydroxyl, amino, nitro, cyano, —CHO, —COOH, oxo, $C_1$-$C_6$alkyl, $C_2$-$C_6$alkenyl, $C_2$-$C_6$alkynyl $C_1$-$C_6$alkoxy, $C_1$-$C_2$haloalkyl, $C_1$-$C_2$haloalkoxy, $C_2$-$C_6$alkanoyl, $C_1$-$C_6$alkylester, —$C_0$-$C_4$alkyl(mono- or di-$C_1$-$C_6$alkylamino), and mono- or di-($C_1$-$C_6$alkyl)carboxamide.

$R^{13}$ is independently chosen at each occurrence from halogen, hydroxyl, amino, nitro, cyano, —CHO, —COOH, oxo, $C_3$-$C_7$cycloalkyl, and phenyl.

BRIEF DESCRIPTION OF THE DRAWINGS

FIG. 1A. Average minimum inhibitory concentration (MIC) values for ciprofloxacin in wild-type strain or strains deficient in either subunit of ExoVII (ΔxseA and ΔxseB), n≥4. Statistical significance was calculated using two-tailed Student's t-test in GraphPad Prism. $^{}P<0.01$. $^{*}P<0.001$. FIG. 1B. Same as in FIG. 1A, except the *E. coli* strains express the quinolone-resistant mutation, GyrA-S83L.

FIG. 2A. Five-fold serially-diluted overnight cultures of wild-type *E. coli* strain or strains deficient in either subunit of ExoVII (ΔxseA and ΔxseB) were spotted onto LB plates containing indicated concentrations of quinolones, ciprofloxacin (Cipro) or nalidixic acid (NA) and incubated at 37° C. overnight. Two technical replicates are shown. FIG. 2B. PCR across the genomic copy of gyrA gene. Strains with wild-type gyrA background generated a 2815-bp product; whereas strains with disrupted genomic gyrA by the zeoR cassette generated a ~550-bp product. These strains also carry a single copy plasmid with a mutated gyrA-S83L, making deletion of the genomic gyrA possible.

FIG. 3A. Transformants with pBAD/Thio (empty vector), pYtopA (encoding YTop1) or pYtopA-R327W (encoding YTop1-R327W) were established in either the wild-type, ΔxseA or ΔxseB strains. Upper panel shows the growth of serial dilutions of pBAD/Thio transformants and pYtopA transformants after induction with 0.2% arabinose for 2 hrs, as well as the uninduced pYtopA-R327W transformants. The lower panel shows the growth of pYtopA-R327W transformants after induction with arabinose for the indicated periods of time. The cultures were spotted on LB plates with 2% glucose and 50 μg/mL carbenicillin and incubated at 37° C. overnight. The dilution of each sample is indicated above the image, and columns of equal spotting densities were indicated by circles. Representative plates of duplicates are shown. FIG. 3B. Growth of pYtopA-R327W transformants under continuous induction with indicated concentrations of arabinose. The indicated strains were spotted on LB plates containing 50 μg/mL carbenicillin and indicated concentrations of arabinose and incubated at 37° C. overnight. The $OD_{600}$ value of each dilution is indicated above the image, and columns of equal spotting densities were indicated by circles. Representative plates of duplicates are shown.

FIG. 4A. The upper strands of all three DNA constructs were internally radio-labeled. The constructs differ only by the terminal chemical group of the 5'-overhangs, phosphate (X═P), hydroxyl (X═OH), or phosphotyrosine (X═Y). Concentrations of ExoVII ranged from 0.033 and 0.1 U/μL. The DNA cleavage products were resolved on a 20% denaturing PAGE. FIG. 4B. ExoVII processes the Y-40 construct [same as in (A)] to generate a 39-nt product bearing a 5'-phosphate. Treatment of ExoVII-generated product with alkaline phosphatase (CIP) removes the 5'-phosphate, as demonstrated by the two 39-nt markers bearing either a 5'-phosphate or 5'-hydroxyl. Note that the oligo bearing an additional phosphate group travels faster in PAGE. FIG. 4C. Scheme of the specific cleavage activity of ExoVII for 5'-tyrosine adducts. The single-stranded overhang regions and the site of ExoVII cleavage are indicated (arrow). FIG. 4D. The length of the 5'-overhangs influences the tyrosyl-nuclease activity of ExoVII. Constructs differed only in the complementary lower strands, resulting in 5'-overhangs of different lengths. Concentration of ExoVII ranged from 0.033 and 0.1 U/μL.

FIG. 5A. Recombinant ExoVII obtained from an independent commercial source (NEB instead of ThermoFisher) were tested in the in vitro cleavage assay. Activity of NEB ExoVII towards six different DNA constructs are shown. The upper strands of all DNA constructs are 40-nt long and internally radio-labeled, as depicted by the diagram. The constructs differ from each other only in the terminal chemical group on the 5'-ends, bearing either a phosphate group (X═P), a hydroxyl group (X═OH), or a phosphotyrosine group (X═Y). The lower complementary strands are either 40-nt or 36-nt long, generating constructs with blunt ends or 4-nt overhangs. Concentration of ExoVII from low to high is 0.033 and 0.1 U/μL. ExoVII shows specific cleavage activity only for the tyrosyl-DNA linkages on the 4-nt 5'-overhangs. FIG. 5B. Comparison of two internally radio-labeled DNA constructs: tyrosyl-DNA linkage on the 4-nt 5'-overhangs (Y-40) or a construct with a longer 5'-overhangs (OH-41), as depicted by the diagram. The structures of the single-stranded overhang regions are shown, and the site of ExoVII cleavage is indicated by an arrow. FIG. 5C. Comparison of ExoVII cleavage activities for Y-40 and OH-41 is shown for reaction time of 3 (upper graph) and 60 (lower graph) mins. In each instance, ExoVII processes Y-40 more efficiently than OH-41, though the difference is moderate.

FIG. 6A. Cleavage activity of ExoVII for tyrosyl-DNA linkages on the 5'-overhangs are compared between constructs of different lengths. All constructs are internally radio-labeled and have the same tyrosyl-DNA linkages on the 5'-overhangs that are 4-nt long. The constructs have different overall lengths, as indicated by the diagram. FIG. 6B. The rates of ExoVII processing for constructs of different lengths are quantified and plotted. Longer constructs with tyrosyl-DNA linkages on the 5'-overhangs (Y-80 and Y-60) are processed more efficiently than the shorter constructs (Y-40 and Y-19).

FIG. 7A. Activity of ExoVII towards six different DNA constructs are shown. The upper strands of all DNA constructs are 36-nt long and internally radio-labeled, as depicted by the diagram. The constructs differ from each other only in the terminal chemical group on the 3'-ends, bearing either a phosphate group (X═P), a hydroxyl group (X═OH), or a phosphotyrosine group (X═Y). The lower complementary strands are either 36-nt or 32-nt long, generating constructs with blunt ends or 4-nt overhangs on the 3'-ends. Concentration of ExoVII from low to high is 0.033 and 0.1 U/μL. ExoVII shows similar cleavage activities for all three constructs with 3'-overhangs, regardless of the terminal chemical groups. FIG. 7B. Activities of ExoVII towards tyrosyl-RNA linkages are compared to tyrosyl-DNA linkages on the 5'-ends. Four different internally radio-labeled 32-nt constructs are generated that each contains a 10-nt piece of 5'-phosphotyrosyl DNA or RNA. The lower complementary strands are either 32-nt or 28-nt long, generating constructs with blunt ends or 4-nt overhangs on the 5'-ends, as depicted by the diagram. Concentration of ExoVII from low to high is 0.05, 0.1 and 0.2 U/μL. ExoVII shows specific cleavage activity for tyrosyl-DNA linkages but not tyrosyl-RNA linkages on the 5'-overhangs. FIG. 7C. Activities of ExoVII towards single-stranded DNA with or without tyrosyl-DNA linkages on the 5'-ends are compared. The 40-nt constructs are internally radiolabeled and bear 15 phosphorothioate bonds on the 3'-ends to prevent 3' to 5' digestion by ExoVII, as depicted by the diagram. Concentration of ExoVII increases 2-fold from left to right and the highest concentration is 0.003 U/μL. ExoVII displays strong single-stranded DNA digestion activity, but the presence of tyrosyl-DNA linkages on the 5'-end has no impact on ExoVII activity.

FIG. 8A. Transformants of a single-copy plasmid bearing the gyrA gene including its endogenous promoter and a C-terminal His-tag (pgyrAHis) were established in either the wild-type, ΔxseA or ΔxseB strains. Immunoblotting of different transformant clones probed with anti-His-tag rabbit monoclonal antibody (Cell Signaling) showed a band only in the transformant clones, corresponding to the molecular weight of GyrA (91.9 kDa). The asterisk denotes a non-specific band. FIG. 8B. Immunoblotting of the same transformants as in FIG. 8A, probed with anti-GyrA antibody (Abcam). FIG. 8C. Five-fold serially diluted overnight cultures of pgyrAHis transformants in either the wild-type, ΔxseA or ΔxseB strains were spotted onto LB-Cm (10 μg/ml) plates containing indicated concentrations of quinolones, ciprofloxacin (Cipro) or nalidixic acid (NA) and incubated at 37° C. overnight. Two technical replicates are shown.

FIG. 9A. Diagram depicting the procedures of the RADAR assay. Exponentially growing *E. coli* cells ($OD_{600}$=0.4) were treated with ciprofloxacin for different lengths of time, then 1 volume of treated cells was directly combined with 4 volumes of 1.25× lysis buffer to avoid reversal of DNA gyrase covalent complexes. The lysates were sonicated then phenol-chloroform extracted twice. The DNA pellets were ethanol precipitated and washed twice with 80% ethanol before air drying. The DNA pellets were resuspended in 8 mM NaOH and DNA concentrations of samples were quantified. Equal amount of DNA of each sample was blotted on PVDF membrane and immunoblotting for protein of interest is carried out. FIG. 9B. Increasing concentration of ciprofloxacin treatment in pgyrAHis transformants leads to higher levels of covalently trapped DNA gyrase on purified genomic DNA. These transformants express a functional GyrA with a His-tag on the C-terminal. Immunoblotting was carried out using anti-His-tag antibody.

FIG. 10A. *E. coli* wild-type (WT) and strains deficient in either subunit of ExoVII, ΔxseA or ΔxseB, were transformed with a single-copy plasmid bearing gyrA with a c-terminal His-tag (pgyrAHis). Each strain was grown to log phase and subjected to 6-hr treatment with ciprofloxacin at 0.5 μg/mL. Bacteria were lysed to extract their genomic DNA. Equal amounts of DNA were spotted onto PVDF membrane and probed with indicated antibodies. Immunoblotting with antibodies for DNA served as a loading control. FIG. 10B. Quantification of trapped $GyrA_{His}$. The intensity of anti-His-tag band from each sample in FIG. 10A was corrected for the amount of input DNA, measured by the intensity of the respective anti-DNA band. The adjusted $GyrA_{His}$ signals were then normalized to the signal of the wild-type strain, set as 1. Statistical significance was calculated using two-tailed Mann-Whitney test in GraphPad Prism. *$P<0.05$, $P<0.01$. FIG. 10**C. Immunoblotting of purified genomic DNA from ciprofloxacin-treated *E. coli*. Samples were either untreated, treated with benzonase or with 1 U/μL of ExoVII at 37° C. for 2 hours before being resolved by tris-glycine-SDS PAGE and probed with anti-His-tag antibodies.

FIG. 11A. The growth of wild-type, ΔxseA or ΔxseB strains with or without ciprofloxacin treatment was compared by measuring the cell densities at different time points. Loss of either xseA or xseB leads to hypersensitivity to ciprofloxacin at as early as 1 hr. FIG. 11B. The pgyrHis transformants in wild type, ΔxseA or ΔxseB strains were treated with 0.5 μg/mL ciprofloxacin for 6 hrs. 100 μL of culture with the indicated densities ($OD_{600}$) above each column on LB-Cm (10 μg/ml) plates and incubated at 37° C. overnight. The resulting number of colonies were counted and noted below the picture of each plate. FIG. 11C. Bar graph of quantification of results for $OD_{600}$ of $10^{-2}$ in FIG. 11B.

FIG. 12A. Diagram depicting how trapped DNA gyrase covalent complexes were generated using a DNA construct radio-labeled on the 3'-ends. FIG. 12B. Addition of ciprofloxacin in the presence of DNA gyrase leads to formation of DNA gyrase covalent complexes, which are trapped at the bottom of the wells and cannot enter the sequencing gel. After 1 hour at 25° C., increasing concentrations of ExoVII were added and the reactions were incubated further at 37° C. for 3 hrs. Under these conditions, ExoVII failed to resolve the intact DNA gyrase covalent complexes, as the amounts of complexes remained unchanged.

FIG. 13A. CPID shows synergistic effect with ciprofloxacin in a quinolone-resistant strain, WT-pgyrA-S83L. FIG. 13B. CPID does not synergize with ciprofloxacin in the quinolone-resistant strains deficient in either subunit of ExoVII. FIG. 13C. In-vitro cleavage assay showing inhibition of ExoVII activity in a dose-dependent manner. Representative gel image and quantification are shown. $IC_{50}$ value was averaged from 5 independent experiments. FIG. 13D. CPID is not toxic to HEK293 or MEF cells as determined by relative confluency of seeded cells after 72-hour treatment at the indicated CPID concentration.

DETAILED DESCRIPTION

Terminology

Figure 1A:
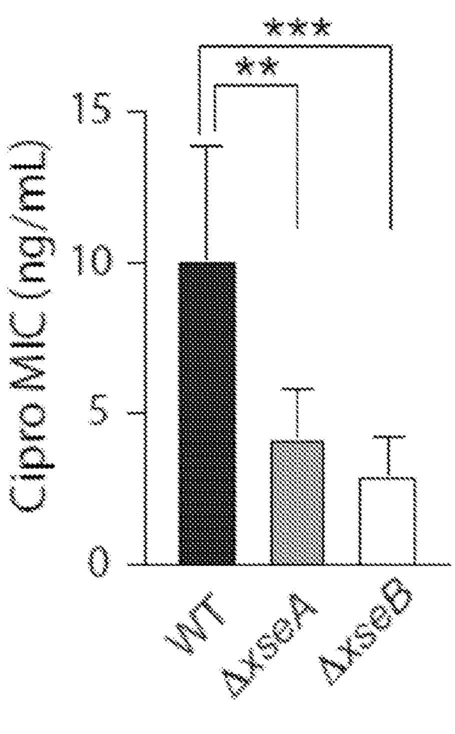
FIG. 1A and FIG. 1B. Loss of exonuclease VII (ExoVII) sensitizes *E. coli* strains with both the wild-type and quinolone-resistant backgrounds to ciprofloxacin (Cipro), which traps prokaryotic type IIA topoisomerases.

In order for the present disclosure to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," or the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. The open-end phrases such as "comprising" include and encompass the close-ended phrases. Comprising may be amended to the more limiting phrases "consisting essentially of" of "consisting of" as needed.

The definition of each expression, e.g., alkyl, m, n, or the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. "H—" is not considered a substituent.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon rings structure are referred to as bicyclic heteroaryl rings.

A "heteroatom" is an atom of any element other than carbon or hydrogen. Illustrative heteroatoms include boron, nitrogen, oxygen, phosphorus, sulfur and selenium.

"Alkyl" is a branched or unbranched aliphatic radical containing the indicated number of carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl. When alkyl is used as part of another term, e.g. ($C_3$-$C_6$cycloalkyl)$C_0$-$C_2$alkyl, it has the definition of "alkyl" given in this paragraph and the point of attachment of the group to the moiety it substitutes is through the alkyl portion. $C_0$alkyl is a single bond.

"Alkanoyl" is an alkyl group as defined herein attached to the group it substitutes via a carbonyl —(C═O)— linkage. The carbonyl is included in the number of carbon atoms in the alkanoyl group. For example, a $C_2$alkanoy group is $CH_3$(C═O)—.

"Alkoxy" is an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkenyl" is a straight or branched hydrocarbon group having the indicated number of carbon atoms and at least one carbon-carbon double bond.

"Alkylamino" is an alkyl group as defined herein, attached to the group it substitutes through an amino (NH) linker. Di-alkylamino groups are attached to the substituted group via a nitrogen linker and each alkyl group is independently chosen.

"Alkylcarboximide" is a $R^1N(R^2)C(═O)$— or —$R^1C(═O)N(R^2)$— group, where $R^1$ is alkyl as defined herein and $R^2$ is hydrogen or alkyl as defined herein and $R^1$ and $R^2$ are independently chosen.

"Alkylester" is an alkyl group as defined herein joined to the group it substitutes through a —C(═O)O— or —OC(═O)— linker.

"Cycloalkyl" is a saturated carbocyclic group having 3 to 7 ring carbon atoms, preferably 3 to 6 ring carbon atoms, or the indicated number of ring carbon atoms. Examples of cycloalkyl groups include cyclopropyl, cyclobutyl, cyclopentyl, and cyclohexyl.

The term "heterocycloalkyl," means a saturated ring group usually having 4- to 7-ring atoms with 1 or 2 ring atoms independently chosen from N, O, and S: Examples of heterocycloalkyl groups includes azepines, azetidinyl, morpholinyl, pyranyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

"Aryl" is an aromatic cyclic group containing only carbon ring atoms such as a phenyl group or a naphthyl group. The aryl groups of the present disclosure can be optionally substituted with 1, 2, 3, 4 or 5 substituents.

"Heteroaryl" is an aromatic cyclic group having one, two, or more fused rings where at least one ring is aromatic, and containing 1, 2, or 3 heteroatoms independently chosen from N, O, and S. Preferred heteroaryl groups have 1 or 2 fused rings, with at least one ring being an aromatic ring containing from 1 to 4 heteroatoms independently chosen from N, O, and S. Monocyclic heteroaryl groups typically have from 5 to 7 ring atoms. In certain embodiments there heteroaryl group is a 5- or 6-membered heteroaryl group having 1, 2, 3, or 4 heteroatoms chosen from N, O, and S, with no more than 2 O atoms and 1 S atom. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

"Halo" or "halogen" means —Cl, —Br, —I or —F.

"Haloalkyl" is an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

"Hydroxyl" means an —OH group.

"Haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy.

"Cyano" is a —C≡N group.

"Nitro" is a $—NO_2$ group.

"Pharmaceutically acceptable salts" includes derivatives of the disclosed compounds wherein the parent compound is modified by making non-toxic acid or base salts thereof, and further refers to pharmaceutically acceptable hydrates or solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like.

The term "carrier" applied to pharmaceutical compositions/combinations of this disclosure, are inactive materials, such as a diluent, excipient, or vehicle with which an active compound is provided. Pharmaceutical compositions meet the U.S. FDA's GMP (good manufacturing practice) standards for human or non-human drugs.

A "therapeutically effective amount" or "effective amount" is that amount of a pharmaceutical agent to achieve a pharmacological effect. The term "therapeutically effective amount" includes, for example, a prophylactically effective amount, that is an amount effective to significantly reduce the probability of occurrence of a disorder in a patient at risk for the disorder. An "effective amount" of topoisomerase IIA inhibitor or Exo VII inhibitor is an amount needed to achieve a desired pharmacologic effect or therapeutic improvement without undue adverse side effects. Effective amounts of topoisomerase IIA inhibitors are generally known as many of these compounds, such as the fluoroquinolone antibiotics, are old in the art. The therapeutically effective amount will be the previously determined effective dose or a lower dose. The effective amount of a topoisomerase type IIA inhibitor or Exo VII inhibitor will also be an amount selected by those skilled in the art depending on the particular patient and the type of conditions being treated. It is understood that "an effective amount" or "a therapeutically effective amount" can vary from patient to patient, due to variation in general condition of the subject, the condition being treated, the severity of the condition being treated, and the judgment of the prescribing physician. When discussing a method of treating a bacterial infection, an effective amount includes an amount effective to have a statistically significant and favorable effect on the systems of infection or an amount effective for the patient to clear the bacterial infection.

The terms "treating" and "treatment" mean implementation of therapy with the intention of reducing in severity or frequency symptoms, elimination of symptoms or underlying cause, prevention of the occurrence of symptoms or their underlying cause, or the improvement or remediation of damage due to a disorder or disease. In certain embodiments "treatment" includes prophylactic treatment, which is administering an amount of the topoisomerase type IIA and ExoVII inhibitor effective to significantly reduce the chance of infection by a microbial pathogen a patient.

Chemical Description

"Formula I" includes compound of Formula I and their pharmaceutically acceptable salts, and compounds falling with subformulae for Formula I and salts thereof.

In certain situations, the compounds of Formula I may contain one or more asymmetric elements such as stereogenic centers, stereogenic axes and the like, e.g. asymmetric carbon atoms, so that the compounds can exist in different stereoisomeric forms. Formula I includes all stereoisomeric forms, including racemates, optically enriched, and optically pure forms. In addition, compounds with carbon-carbon double bonds may occur in Z- and E-forms, with all isomeric forms of the compounds being included in the present disclosure. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The disclosure of the compounds of Formula I includes all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$ and isotopes of fluorine including $^{19}F$.

Certain compounds are described herein using a general formula that includes variables, e.g. $Y^1$, $Y^2$, and $R^1$-$R^2$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone.

Combinations of substituents and/or variables are permissible only if such combinations result in stable compounds. A stable compound or stable structure is meant to imply a compound that is sufficiently robust to survive isolation from a reaction mixture, and subsequent formulation into an effective therapeutic agent.

Exo VII Inhibitors

This disclosure includes compounds of Formula I and pharmaceutically acceptable salts thereof.

Formula (I)

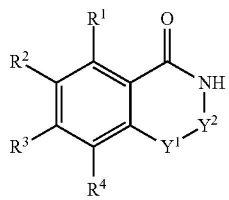

In certain embodiments the variables in Formula (I), carry the following definitions:

$Y^1$ is carbon substituted with oxo and $Y^2$ is $CR^6$; or $Y^1$ is $CR^5$ and $Y^2$ is carbon substituted with oxo;

$R^1$, $R^3$, and $R^4$ are independently chosen from H, halogen, hydroxyl, amino, nitro, cyano, $C_1$-$C_4$alkyl, $C_1$-$C_4$alkoxy, $C_1$-$C_2$haloalkyl, and $C_1$-$C_2$haloalkoxy;

$R^2$ is H, halogen, hydroxyl, amino, nitro, cyano, —COOH, $C_1$-$C_4$alkyl, $C_1$-$C_4$alkoxy, $C_1$-$C_2$haloalkyl, or $C_1$-$C_2$haloalkoxy; or $R^2$ is —$C_0$-$C_2$alkyl($C_3$-$C_7$cycloalkyl), —$C_0$-$C_2$alkyl(aryl), —$C_0$-$C_2$alkyl(pyridyl), or —$C_0$-$C_2$alkyl(furanyl), each of which is optionally substituted with one or more substituents independently chosen from $R^{10}$;

$R^4$ is H, halogen, hydroxyl, amino, nitro, cyano, $C_1$-$C_4$alkyl, $C_1$-$C_4$alkoxy, $C_2$-$C_6$alkanoyl, —$C_1$-$C_6$alkylester, —$C_0$-$C_4$alkyl(mono- or di-$C_1$-$C_6$alkylamino), mono- or di-$C_1$-$C_6$alkylcarboxamide; $C_1$-$C_2$haloalkyl, or $C_1$-$C_2$haloalkoxy;

$R^5$ and $R^6$ are independently chosen from H, halogen, hydroxyl, amino, nitro, cyano, —CHO, —COOH, —$CONH_3$, $C_1$-$C_4$alkyl, $C_1$-$C_4$alkoxy, $C_1$-$C_2$haloalkyl, $C_1$-$C_2$haloalkoxy, $C_2$-$C_6$alkanoyl, $C_1$-$C_6$alkylester, —$C_0$-$C_4$alkyl(mono- and di-$C_1$-$C_6$alkylamino), and mono- and di-($C_1$-$C_6$alkyl)carboxamide;

$R^{10}$ is independently selected at each occurrence from halogen, hydroxyl, amino, nitro, cyano, —CHO, —COOH, oxo, $C_1$-$C_8$alkyl, $C_2$-$C_8$alkenyl, and $C_2$-$C_8$alkynyl, wherein in each $C_1$-$C_8$alkyl, $C_2$-$C_8$alkenyl, and $C_2$-$C_8$alkynyl, in the definition of $R^{10}$ one or more carbon atoms is optionally replaced by O, $NR^{11}$, —C(O)—, —$NR^{11}$C(O)—, —C(O)$NR^{11}$—, —C(O)O—, —OC(O)—, —$S(O)_n$—, —$S(O)_nNR^{11}$—, or —$NR^{11}S(O)_n$—, where n is 0, 1, or 2, and in which each $C_0$-$C_4$alkyl, $C_1$-$C_8$alkyl, $C_2$-$C_8$alkenyl, or $C_2$-$C_8$alkynyl is optionally substituted with one or more substituents $R^{13}$;

$R^{11}$ is independently chosen at each occurrence from hydrogen, $C_1$-$C_6$alkyl, and —$C_0$-$C_2$alkyl($C_3$-$C_7$cycloalkyl); and $R^{13}$ is independently chosen at each occurrence from halogen, hydroxyl, amino, nitro, cyano, —CHO, —COOH, oxo, $C_3$-$C_7$cycloalkyl, and phenyl.

The compound of Formula I can be a compound or pharmaceutically acceptable salt of Formula I-A (Formula I-A)

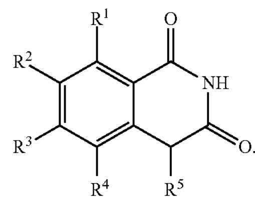

In Formula I-A the variables $R^1$-$R^5$ can have the values above.

The disclosure also includes compounds and salts of Formula I-A in which $R^1$, $R^3$, $R^4$, and $R^5$ are each independently chosen from H and methyl; and $R^2$ is phenyl, furanyl, or pyridyl each of which is optionally substituted with one or more substituents independently chosen from $R^{10}$.

The disclosure also includes compounds and salts of Formula I-A in which $R^1$, $R^3$, $R^4$, and $R^5$ are each independently chosen from H and methyl; and $R^2$ is phenyl, furanyl, or pyridyl each of which is optionally substituted with one or more substituents independently chosen from $R^{10}$ and 0 or 1 substituents $R^{12}$.

The disclosure also includes compounds and salts of Formula I-A in which $R^1$, $R^2$, and $R^4$ are independently chosen from H and methyl; $R^3$ is H, halogen, hydroxyl, or nitro; and $R^5$ is H or $C_1$-$C_6$alkylester; where one of $R^3$ and $R^5$ is other than H.

The compound of Formula I can be a compound or pharmaceutically acceptable salt of Formula I-B (Formula I-B)

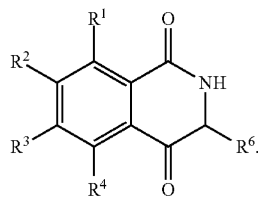

The compound of Formula I can be a compound or pharmaceutically acceptable salt of Formula I-B in which $R^1$, $R^2$, $R^3$, and $R^4$ are independently chosen from H and methyl; and $R^6$ is —$CONH_3$, —COOH, $C_1$-$C_6$alkyl ester, or $C_1$-$C_6$alkylcarboxamide.

Formula I includes the following compounds and their pharmaceutically acceptable salts.

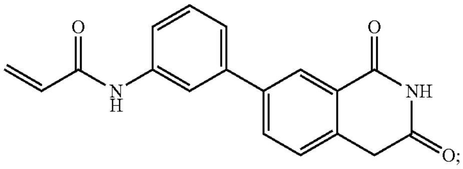
;
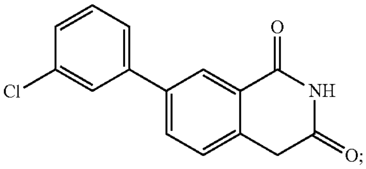
;
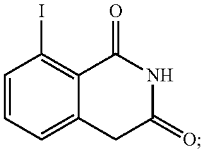
;
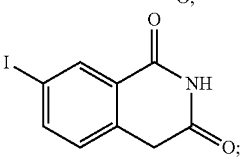
;
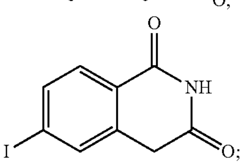
;
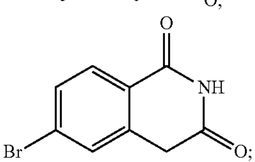
;
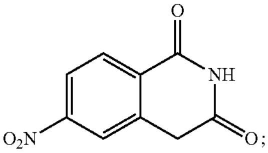
;
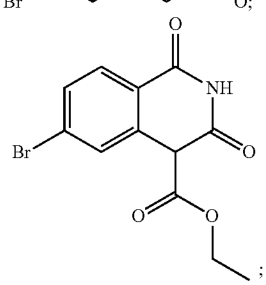
;
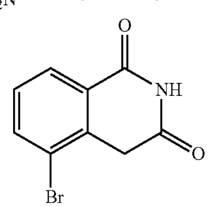
;
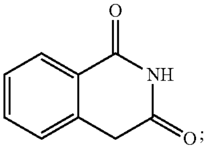
; and
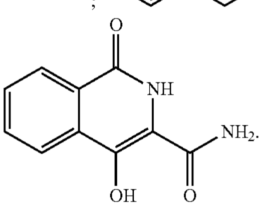
.

Methods of Treatment

This disclosure includes a method of treating or preventing a bacterial infection in a subject comprising administering a therapeutically effective amount of a combination of a bacterial type IIA topoisomerase inhibitor and a bacterial Exonuclease VII (ExoVII) inhibitor to the subject.

"Type IIA topoisomerase inhibitors" include quinolone and fluroquinolone antibiotics such as alatrofloxacin, besifloxacin, cinoxacin, ciprofloxacin, cinoxacin, clinafloxacin, delafloxacin, enoxacin, fleroxacin, finafloxacin, gatifloxacin, gemifloxacin, garenoxacin, grepafloxacin, lomefloxacin, levofloxacin, moxifloxacin, nadifloxacin, nalidixic acid, norfloxacin, pazufloxacin mesylate, prulifloxacin, ofloxacin, perfloxacin, rufloxacin, sparfloxacin, temafloxacin, and trovafloxacin.

ExoVII inhibitors include, at least, compounds of Formula I and subformulae of Formula I (Formula I-A and I-B) and the pharmaceutically acceptable salts of any of the foregoing.

Treatment of human patients is particularly contemplated. However, treatment of non-human subjects is within the scope of the disclosure. The disclosure includes treatment or prevention of microbial infections in fish, amphibians, reptiles or birds, but a preferred embodiment of the disclosure includes treating mammals, such as rodents (rats, guinea pigs), companion animals (e.g. cats, dogs), or livestock animals (sheep, goats, pigs, cattle, horses).

The bacterial infection can be an antibiotic-tolerant or antibiotic-resistant infection. The bacterial infection can be caused by a Gram-negative bacterium, Gram-positive bacterium, or *Mycobacterium.*

In an embodiment of any of the methods of this disclosure, the microbial infection is the result of a pathogenic bacterial infection. Examples of pathogenic bacteria include, without limitation, bacteria within the genera Aerobacter, *Aeromonas, Acinetobacter, Agrobacterium, Bacillus, Bacteroides, Bartonella, Bordetella, Brucella, Burkholderia, Calymmatobacterium, Campylobacter, Citrobacter, Clostridium, Corynebacterium, Enterobacter, Enterococcus, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio*, and *Yersinia*. Specific examples of such bacteria include *Vibrio harveyi, Vibrio cholerae, Vibrio parahemolyticus, Vibrio alginolyticus, Pseudomonas phosphoreum, Pseudomonas aeruginosa, Yersinia enterocolitica, Escherichia coli, Salmonella typhimurium, Haemophilus influenzae, Helicobacter pylori, Bacillus subtilis, Borrelia burgdorferi, Neisseria meningitidis, Neisseria gonorrhoeae, Yersinia pestis, Campylobacter jejuni, Mycobacterium tuberculosis, Enterococcus faecalis, Streptococcus pneumoniae, Streptococcus pyogenes, Klebsiella pneumoniae, Burkholderia cepacia, Acinetobacter baumannii, Staphylococcus epidermidis*, and *Staphylococcus aureus.*

In some embodiments, the bacterial infection is a Gram-negative bacterium, such as an Enterobacteriaceae, e.g., *Klebsiella pneumonia*, e.g., *Escherichia coli*, e.g., *Enterobacter cloacae*, e.g., *Serratia marcescens*, e.g., *Salmonella typhimurium*, e.g., *Shigella dysenteriae*, e.g., *Proteus mirabilis*, e.g., *Citrobacter freundii*, e.g., *Yersinia pestis.*

In some embodiments, the bacterial infection is a Gram-positive bacterium, such as e.g. *S. pneumonia*, e.g., *S. aureus*, e.g., *S. epidermidis*, e.g., *M. mucogenicum.*

In some embodiments, the infection is a polymicrobial infection, e.g., an infection comprising more than one organism. In some embodiments, the infection comprises at least one of the organisms listed above, e.g., one or more of *Pseudomonas*, e.g., *P. aeruginosa, Klebsiella*, e.g., *Klebsiella pneumoniae*, and/or *Acinetobacter*, e.g., *A. baumannii.*

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition/combination may contain a compound or salt of Formula I as the only active agent or may be combined with one or more additional active agents. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of type IIA topoisomerase and an Exo VII inhibitor.

Compounds disclosed herein may be administered orally, topically, parenterally, by inhalation or spray, sublingually, transdermally, via buccal administration, or by other means routine in the art for administering pharmaceutical compositions. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of a type IIA topoisomerase and Exo VII inhibitor and usually at least about 5 wt. % of a compound of Formula I. Some embodiments contain from about 25 wt. % to about 50 wt. % or from about 5 wt. % to about 75 wt. % of the two inhibitors.

Examples

Exo VII Inhibitor Activity

Applicants have discovered bacterial Exonuclease VII (ExoVII) functions as a repair enzyme for type IIA topoisomerases that have been trapped by the widely used class of quinolone antibiotics. Consequently, inactivation of ExoVII leads to hypersensitivity to bacterial type IIA topoisomerase inhibitors, such as quinolones. Applicants' screen for ExoVII inhibitors revealed a class of isoquinolinedione derivatives of Formula I, which synergizes with ciprofloxacin in only wild-type strains and not in strains deficient in ExoVII, suggesting that they specifically inhibit ExoVII in culture. Certain of these compounds were previously reported as inhibitors for tyrosyl DNA-phosphodiesterase 2 (TDP2), which is the analogous repair enzyme for trapped type IIA topoisomerases in eukaryotes. However, these compounds were not effective for TDP2 inhibition in culture, contrary to the ExoVII inhibitory effect in *E. coli*. Applicants confirmed that Formula I isoquinolinedione compounds inhibit recombinant ExoVII in vitro and that they are not harmful to cultured human cells.

We have determined that ExoVII, a multimeric complex composed of a catalytic subunit, XseA (encoded by xseA) and regulatory subunits, XseB (encoded by xseB) acts as a repair nuclease for trapped topoisomerases in bacteria. We assessed quinolone hypersensitivity of ExoVII-deficient *E. coli* strains by measuring the minimum inhibitory concentration (MIC) of ciprofloxacin (FIG. TA and FIG. 2A). Deficiency in either subunit of ExoVII (ΔxseA or ΔxseB) decreased the MIC of ciprofloxacin to 30-40% of wild-type strains. Importantly, ExoVII-deficient strains are not hypersensitive to non-quinolone topoisomerase catalytic inhibitor, suggesting that ExoVII is specifically involved in repairing DNA gyrase TOPcc rather than damage stemming from the loss of DNA gyrase.

Figure 1B:
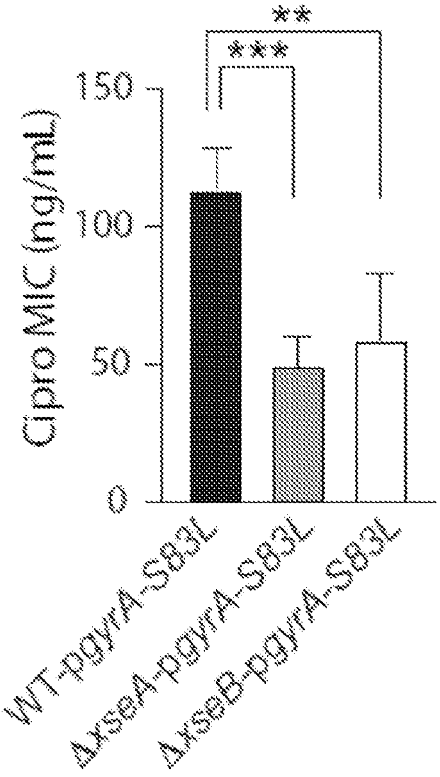
Figure 2A:
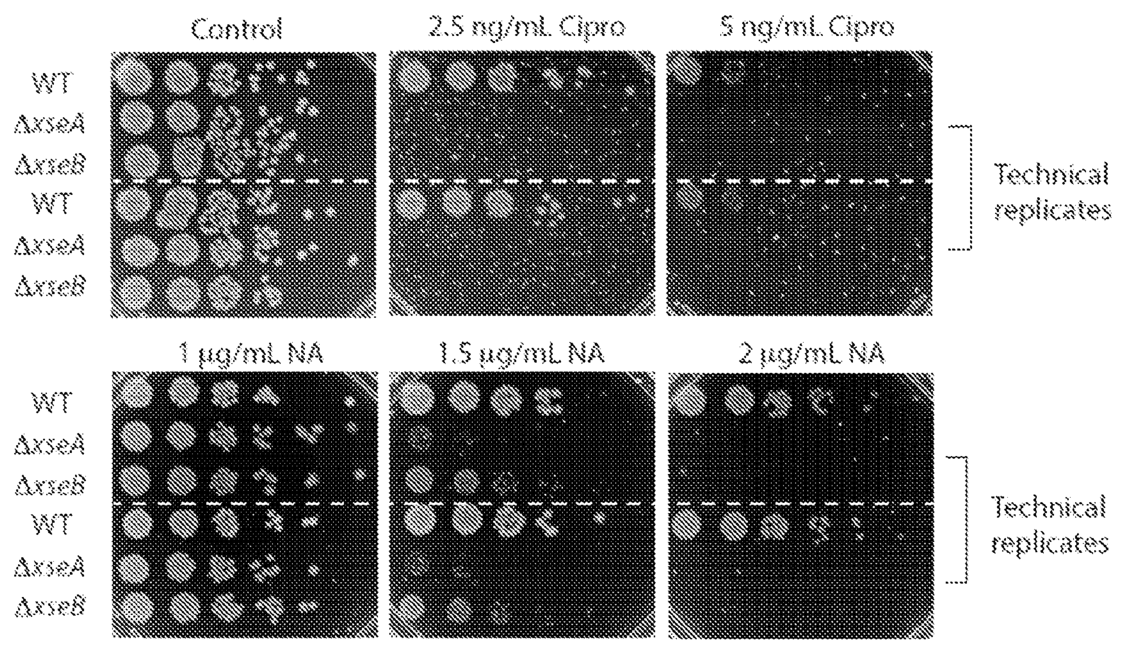
FIG. 2A and FIG. 2B. Loss of exonuclease VII (ExoVII) sensitizes *E. coli* strains of both the wildtype and quinolone-resistant backgrounds to quinolone treatment.
Figure 2B:
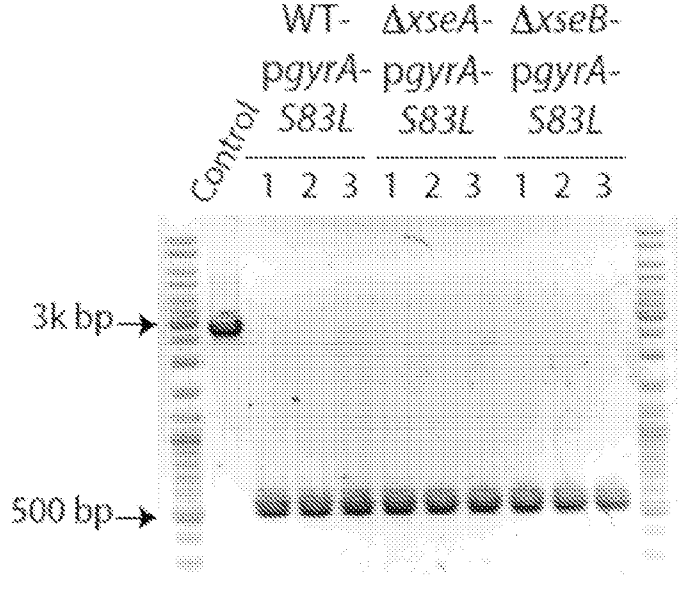

Quinolone-resistant bacterial strains in the clinical settings frequently feature mutations at the quinolone binding pocket of GyrA (the catalytic subunit of DNA gyrase). One leading recurrent mutation is gyrA-S83L. To determine whether inactivating ExoVII in a quinolone-resistant strain can re-sensitize the bacteria to quinolones, we generated *E. coli* strains carrying the gyrA-S83L mutation on a single-copy plasmid (pgyrA-S83L) followed by inactivation of the genomic gyrA (FIG. 2B). As expected, gyrA-S83L led to resistance to ciprofloxacin, reflected in a 10-fold increase in ciprofloxacin MIC (FIGS. 1A and 1B). Inactivating either subunit of ExoVII in this background decreased the ciprofloxacin MIC by ~2-fold (FIG. 1B).

Figure 3A:
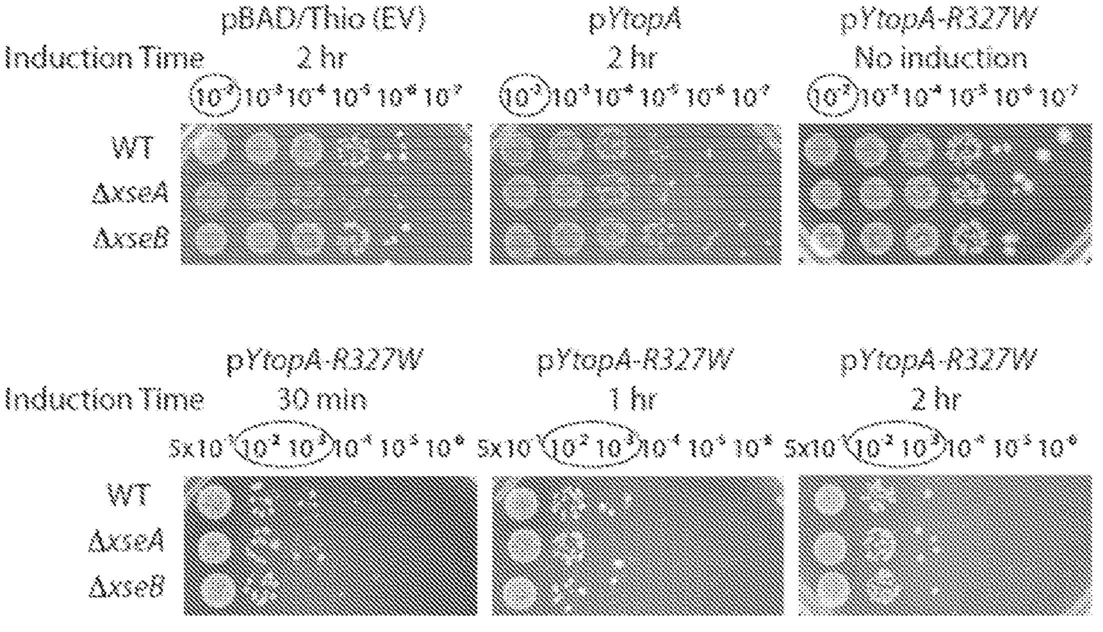
FIG. 3A and FIG. 3B. Loss of ExoVII does not sensitize the cells to trapped type IA topoisomerases.
Figure 3B:
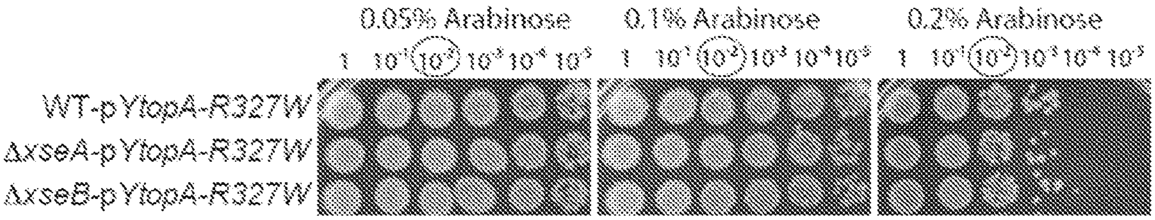

Next, we examined whether ExoVII also plays a role in repairing TOPcc induced by the other major topoisomerases in prokaryotes, type IA topoisomerases. Due to lack of known inhibitors for type IA topoisomerases, we employed a set of plasmids under the control of the arabinose-inducible BAD promoter, carrying either wild-type *Yersinia pestis* topoisomerase I (YTop1) or a mutated YTop1-R327W that leads to accumulation of covalently-linked type IA topoisomerase. After establishing transformants in the wild-type, ΔxseA and ΔxseB *E. coli* strains, we induced the expression of either empty vector, wild-type YTop1, or YTop1-R327W. Induction of the control empty vector and wild-type YTop1 showed comparable growth to the uninduced cells (FIG. 3A). By contrast, induction of YTop1-R327W decreased survival rates by more than 1000-fold (FIG. 3A), confirming the detrimental effects of YTop1-R327W expression. Nevertheless, we did not observe any difference in survival rates between the wild-type and ExoVII-deficient strains. We also did not observe any difference between the wild-type and ExoVII-deficient strains when YTop1-R327W was continuously induced by arabinose (FIG. 3B). These results suggest that ExoVII plays a role in the repair of the trapped type IIA but not type IA topoisomerases.

Figure 4A:
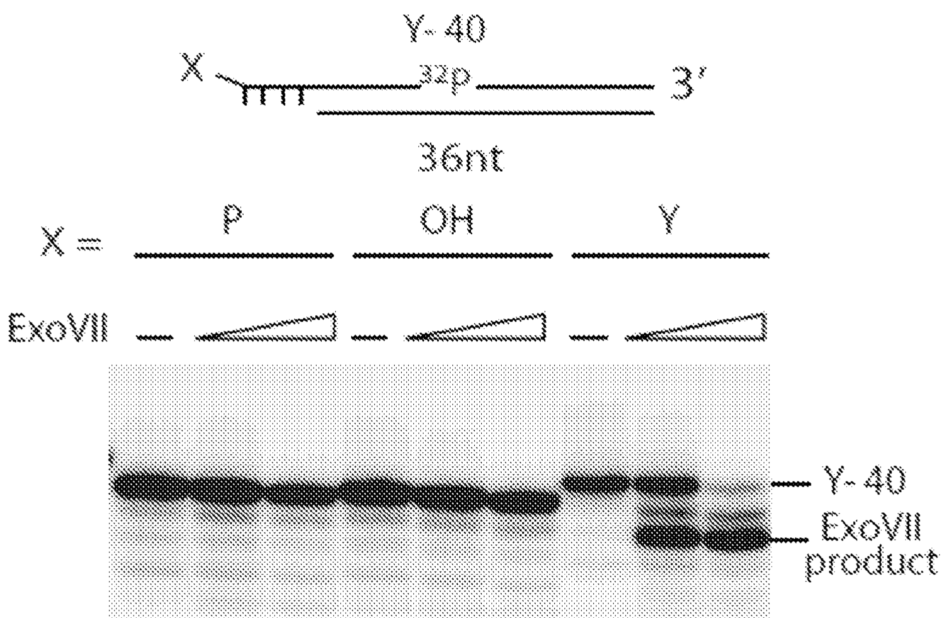
FIG. 4A, FIG. 4B, FIG. 4C, and FIG. 4D. Recombinant ExoVII selectively cleaves tyrosyl-DNA linkages on 5'-overhangs.
Figure 4B:
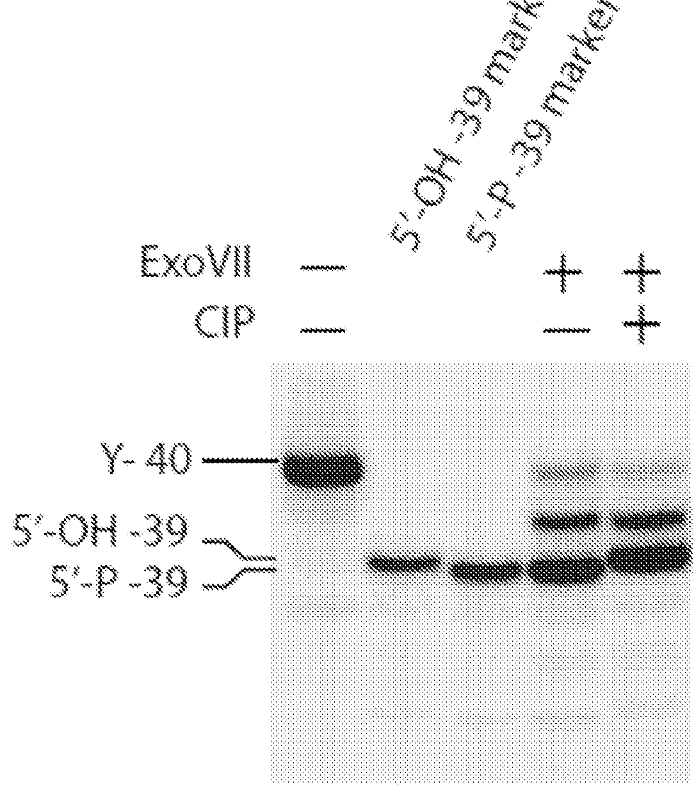
Figure 4C:
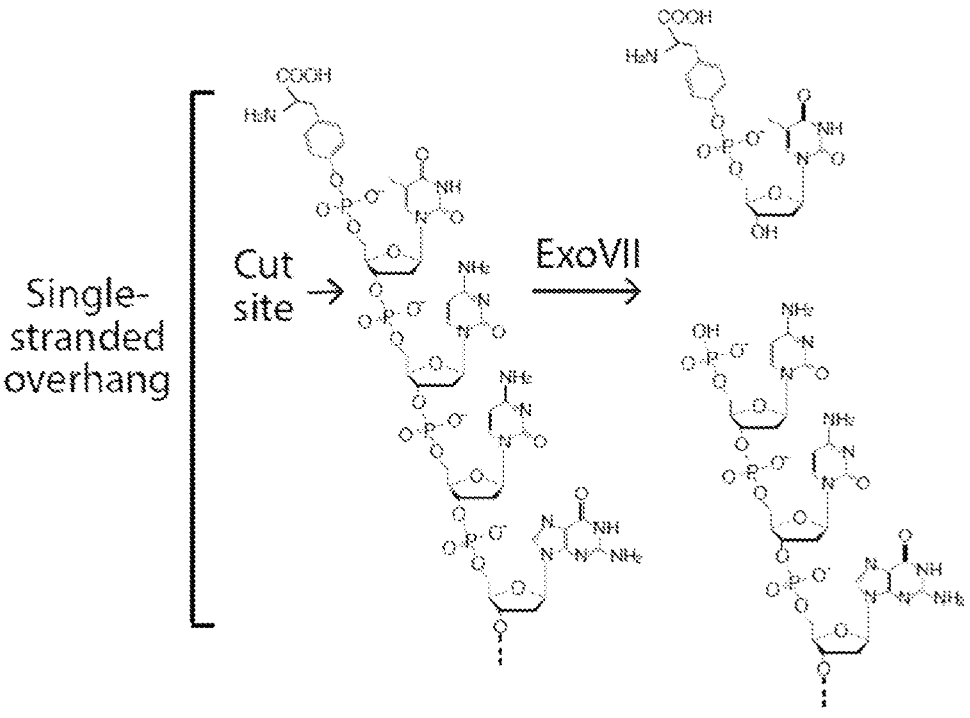

We next tested whether ExoVII could act like eukaryotic TDP enzymes and excise tyrosyl-DNA linkages in biochemical assays. DNA substrates were internally radiolabeled and contained phosphorothioate linkages at the 3'-ends to specifically track the potential excision activity of ExoVII for DNA 5'-ends. We found that ExoVII was capable of removing the tyrosine adduct from a 4-nt overhang on the 5'-end of DNA (Y-40, mimetic of trapped type IIA topoisomerase) (FIG. 4A). This DNA cleavage activity was specific for 5'-end tyrosine, as ExoVII was not able to efficiently cleave constructs bearing 5'-phosphate or 5'-hydroxyl groups (FIG. 4A). Further analysis showed that ExoVII processed the Y-40 substrate to a 39-nt product with a 5'-phosphate group (FIG. 4B). This was confirmed by treating the ExoVII cleavage product with alkaline phosphatase (CIP), which resulted in an upper shift (FIG. 4B), corresponding to the conversion of the terminal 5'-phosphate group to a 5'-hydroxyl group. The structures of the DNA constructs and ExoVII specific cut site are shown in FIG. 4C.

Figure 4D:
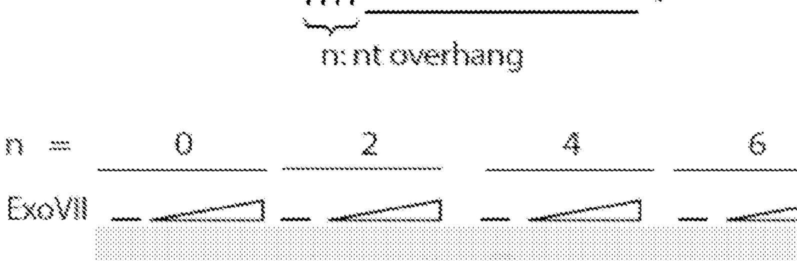
Figure 4D:
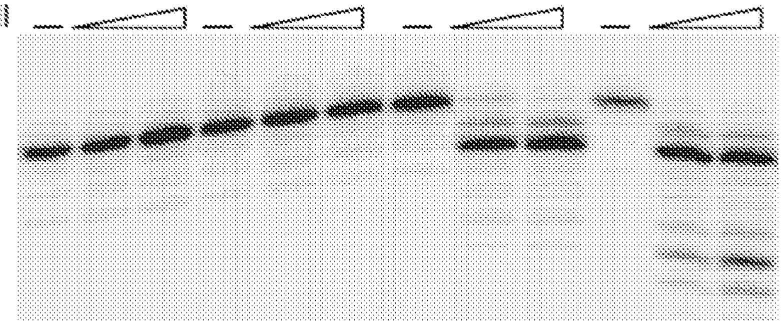
Figure 5A:
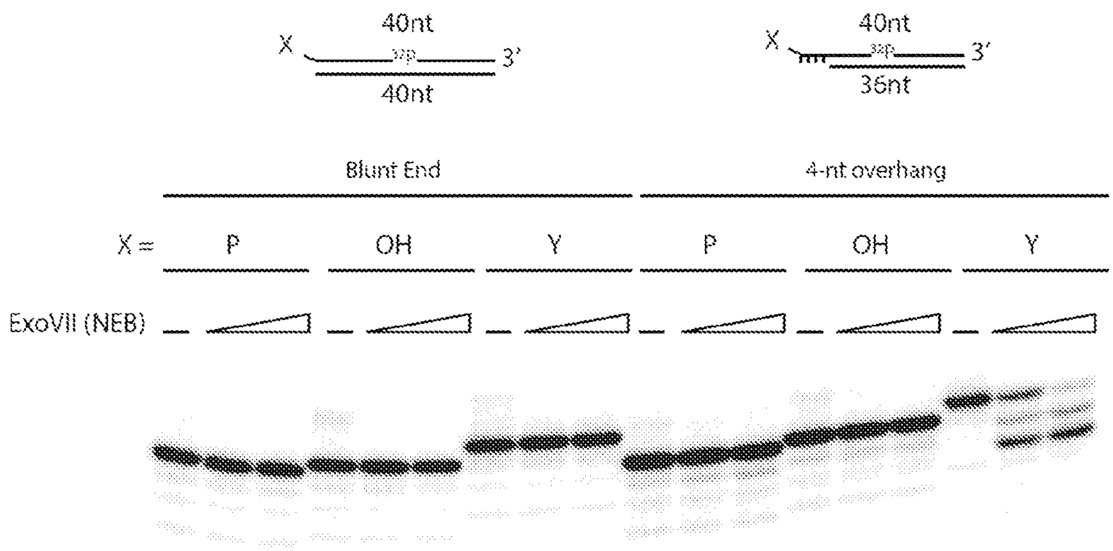
FIG. 5A, FIG. 5B, and FIG. 5C. Recombinant ExoVII shows consistent biochemical cleavage activity for tyrosyl-DNA linkages on 5'-overhangs of DNA.

Varying the length of overhangs showed that ExoVII requires at least 4-nt overhang for its tyrosine removal activity. In particular, ExoVII generated the same specific products from substrates with either 4-nt or 6-nt overhangs, although some non-specific activity was observed in substrates with longer overhangs (FIG. 4D). On the other hand, ExoVII was inactive for substrates with 2-nt overhangs or blunt ends (FIG. 4D). As the ExoVII tested was obtained from a commercial source, we verified that ExoVII from another independent source displayed equivalent activities (FIG. 5A).

Figure 5B:
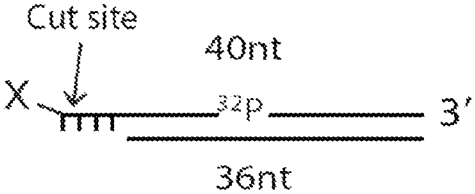
Figure 5B:
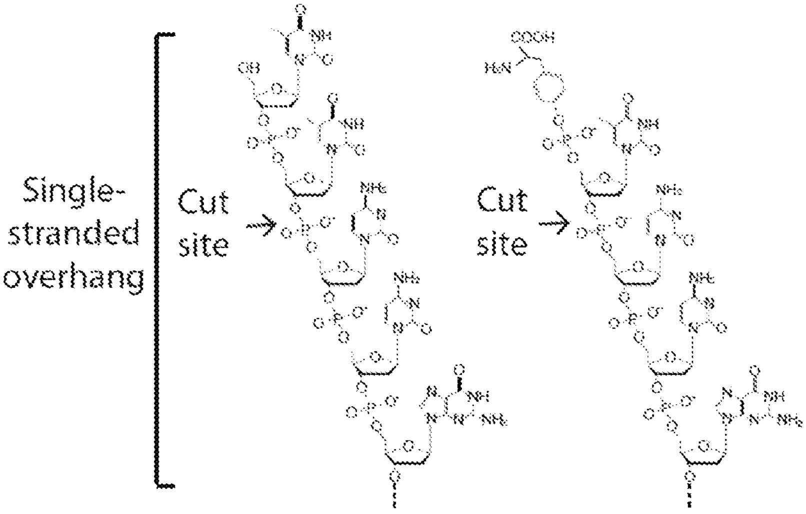
Figure 5C:
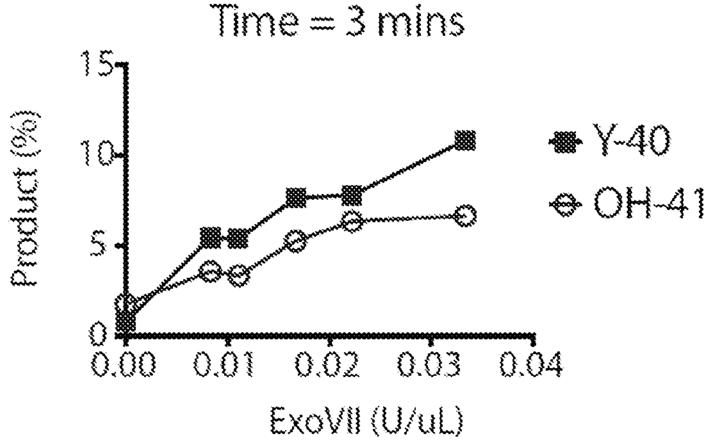
Figure 5C:
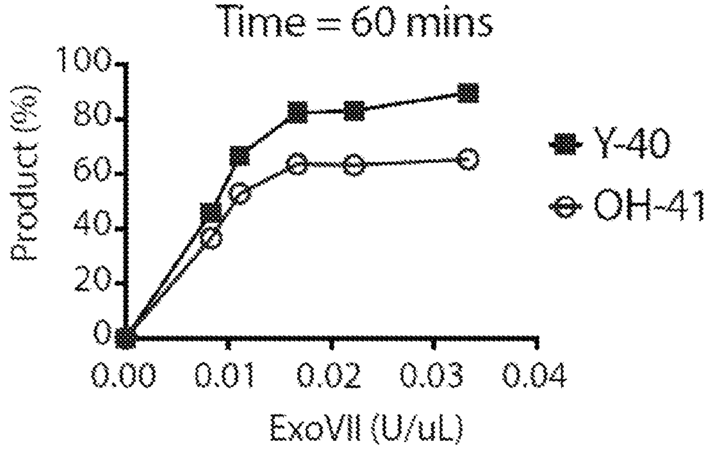
Figure 6A:
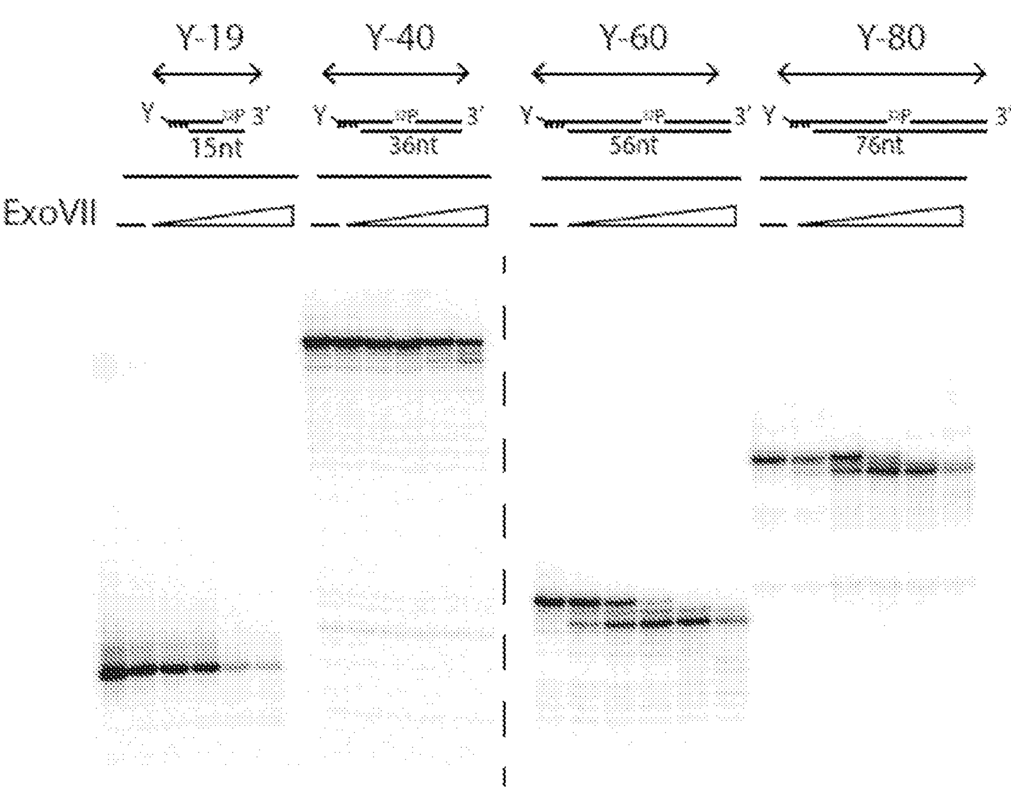
FIG. 6A and FIG. 6B. Long double-stranded regions of DNA facilitate the tyrosyl-DNA cleavage activities of ExoVII on 5'-overhangs.
Figure 6B:
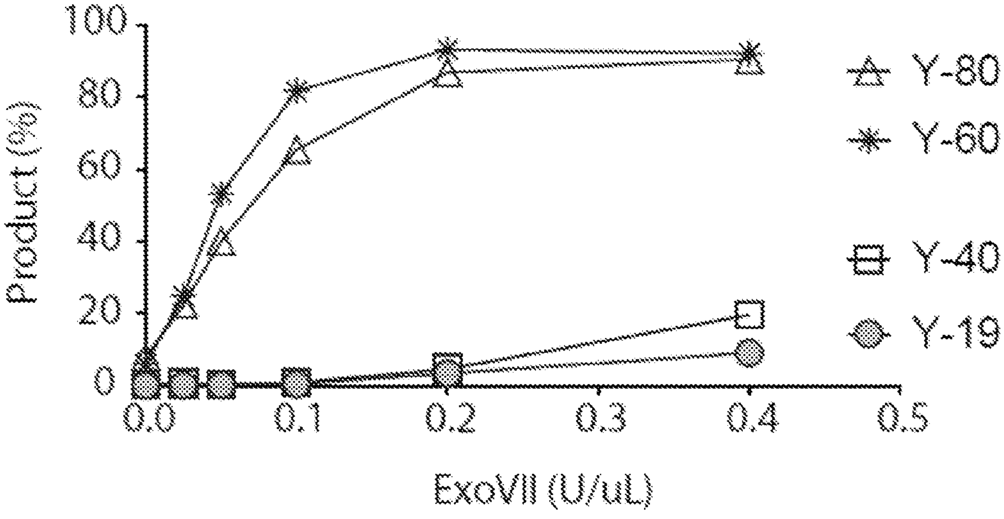
Figure 7A:
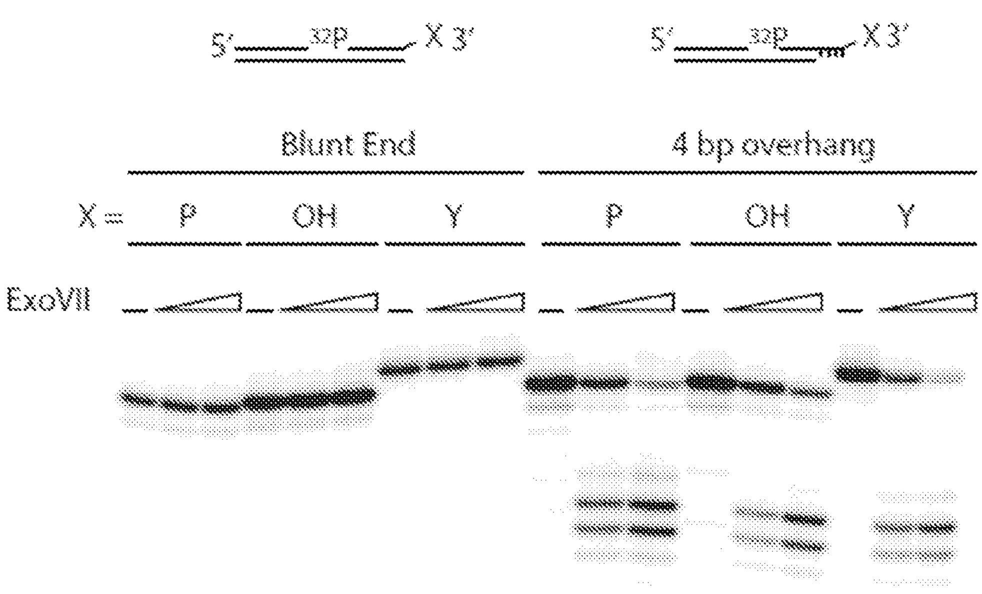
FIG. 7A, FIG. 7B, and FIG. 7C. ExoVII does not have specific cleavage activity for tyrosyl-DNA linkages on 3'-overhangs of DNA, nor on 5'-overhangs of RNA, nor on 5'-end of single-stranded DNA.
Figure 7B:
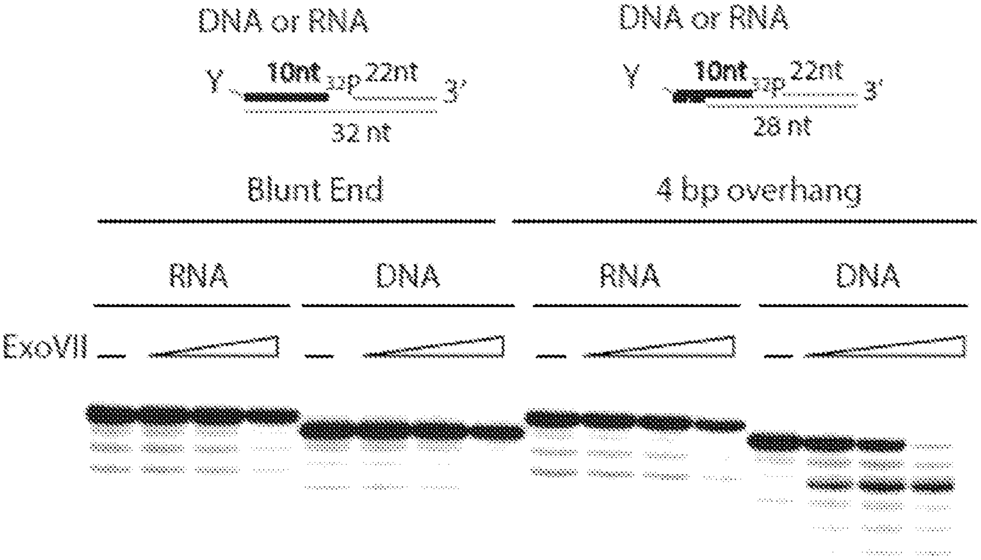
Figure 7C:
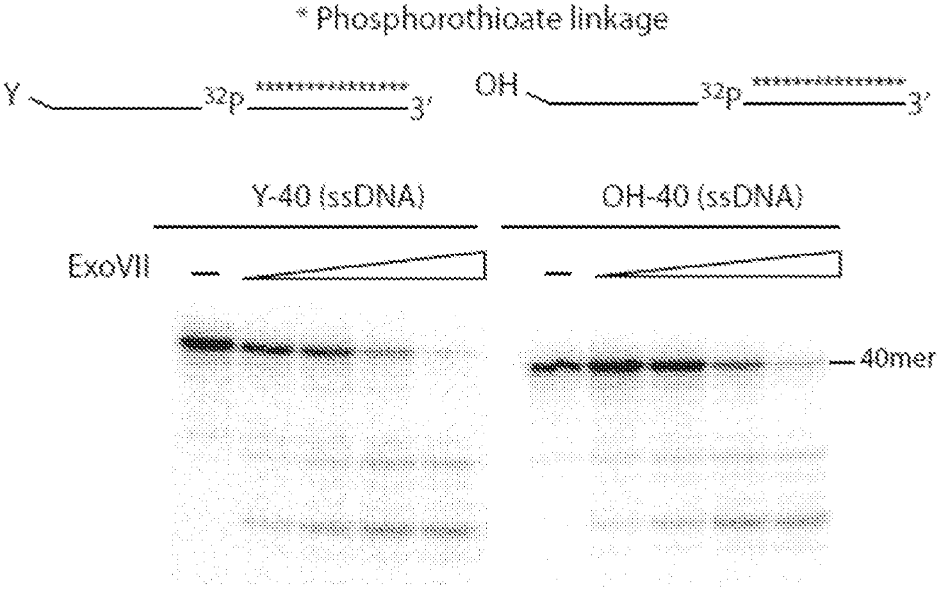

We compared ExoVII's activity for the tyrosine adducts on 5'-overhangs with an overhang of comparable length. ExoVII consistently processed the tyrosine adducts more efficiently (FIG. 5B-5C), indicating that tyrosine on 5'-overhang confers important substrate specificity for ExoVII. We also compared ExoVII activity for DNA constructs of varying lengths. The tyrosyl nuclease efficiencies of ExoVII increased with longer DNA constructs (FIG. 6A-6B), suggesting that ExoVII binds and scans the DNA to locate its cleavage substrates. To further define the substrate specificity of ExoVII, we tested tyrosine adducts on the 3'-DNA overhangs, where the tyrosine moiety conferred no effect on ExoVII activity (FIG. 7A). This appears consistent with the fact that type IB topoisomerases, the only known enzyme that generates 3'-tyrosyl-DNA linkages, are absent from the bacterial domain with the exception of a handful of species. Because type IA topoisomerases can act as RNA topoisomerases, we also tested activity of ExoVII for tyrosine adducts on 5'-overhangs of RNA. However, we did not detect any ExoVII activity for tyrosine-RNA linkages (FIG. 7B). Finally, because ExoVII is known to cleave single-stranded DNA, we compared ExoVII processing efficiency of single-stranded DNA with or without the 5'-tyrosine adducts and found that ExoVII was similarly active for both substrates (FIG. 7C).

Figure 8A:
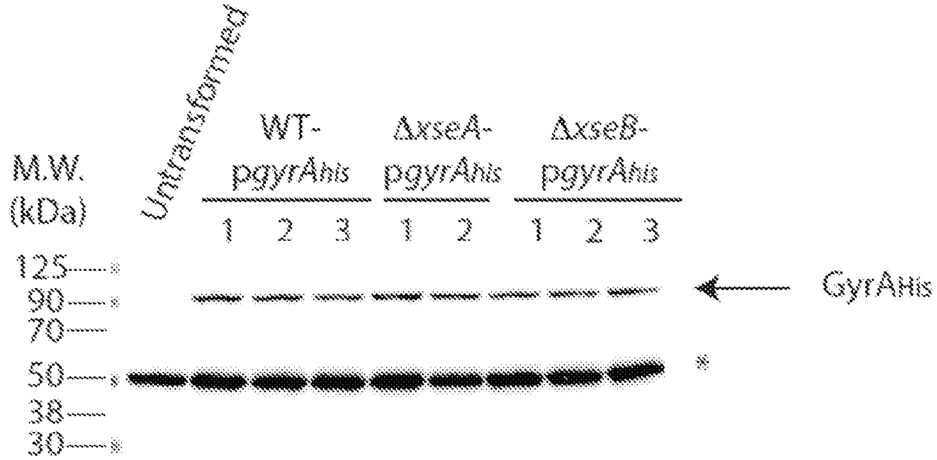
FIG. 8A, FIG. 8B, and FIG. 8C. Expression of a functional $GyrA_{His}$ has no impact on sensitivities of *E. coli* strains to quinolones.
Figure 8B:
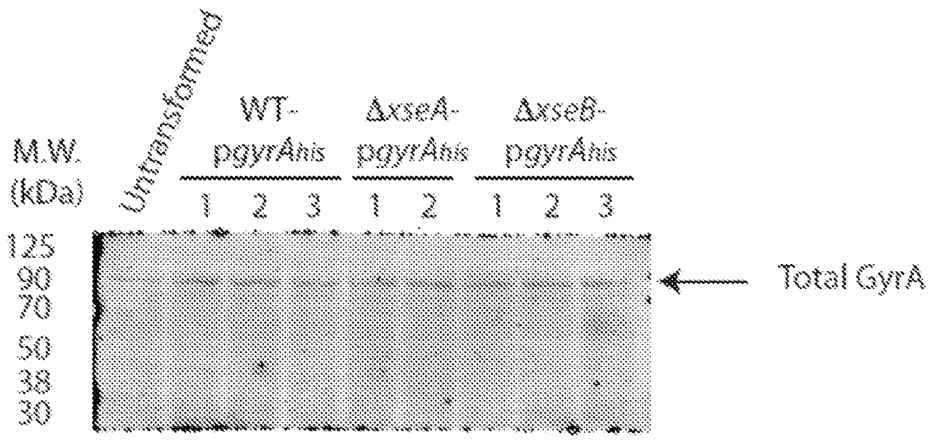
Figure 8C:
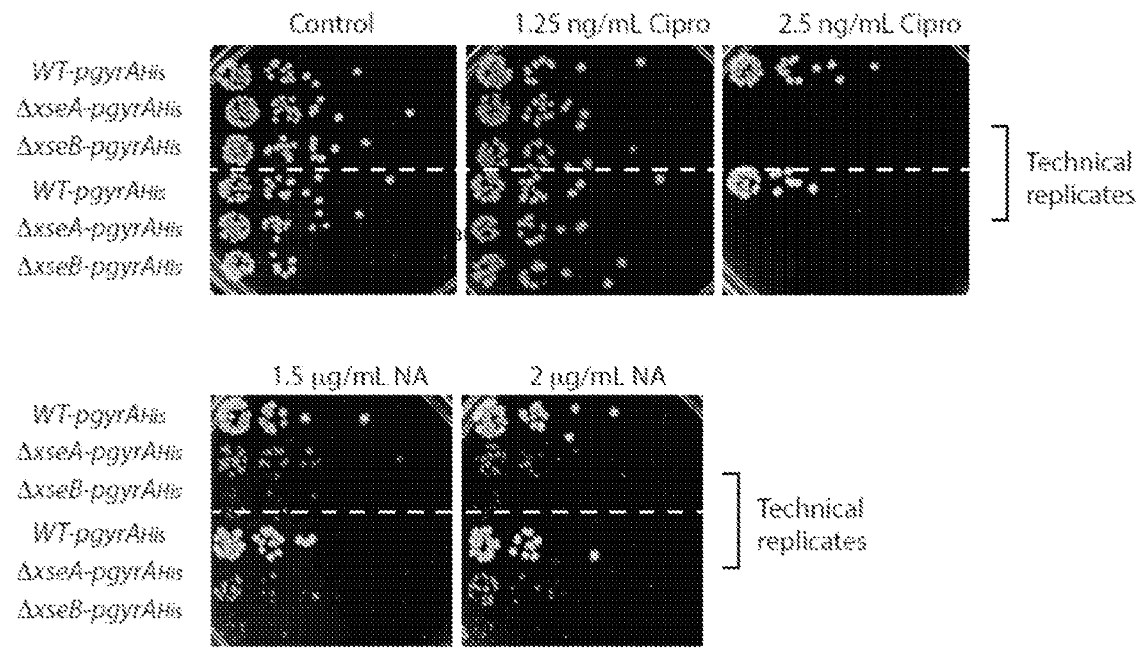

We reasoned that inactivating ExoVII would lead to the accumulation of trapped DNA gyrase on bacterial genomic DNA in vivo. To detect trapped DNA gyrase in vivo, we first constructed a single-copy plasmid carrying the gyrA gene with a C-terminal His-tag (pgyr$A_{His}$). Transformants with pgyr$A_{His}$ were established in wild-type, ΔxseA and ΔxseB *E. coli* strains. As expected, His-tagged GyrA was detected only in the transformants (FIG. 8A), with total levels of GyrA close to the endogenous level in the wild-type strain (FIG. 8B). The transformants deficient in ExoVII displayed similar hypersensitivity to two quinolones (ciprofloxacin and nalidixic acid) (FIGS. 2A and 8C).

Figure 9A:
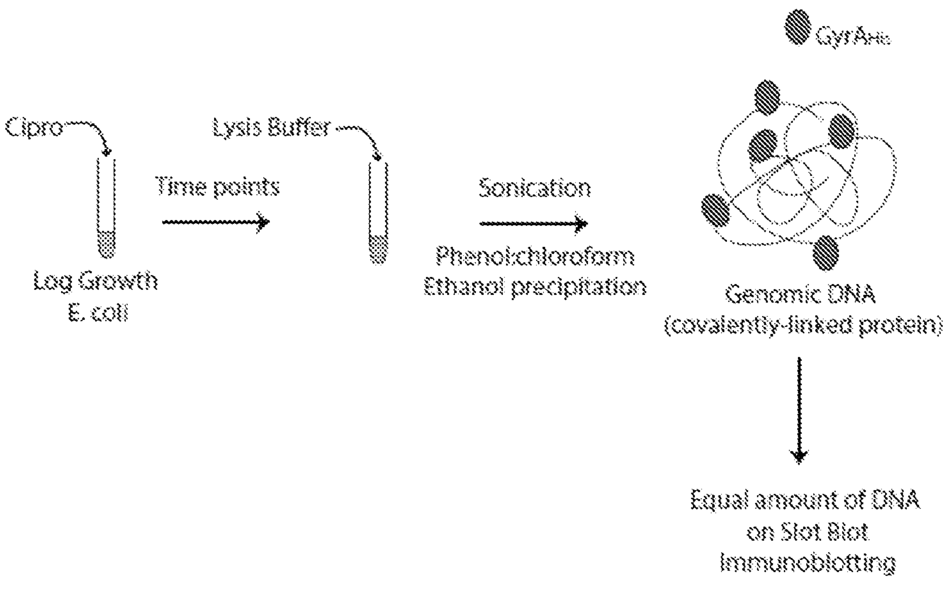
FIG. 9A and FIG. 9B. Rapid approach to DNA adduct recovery (RADAR) assay.
Figure 9B:
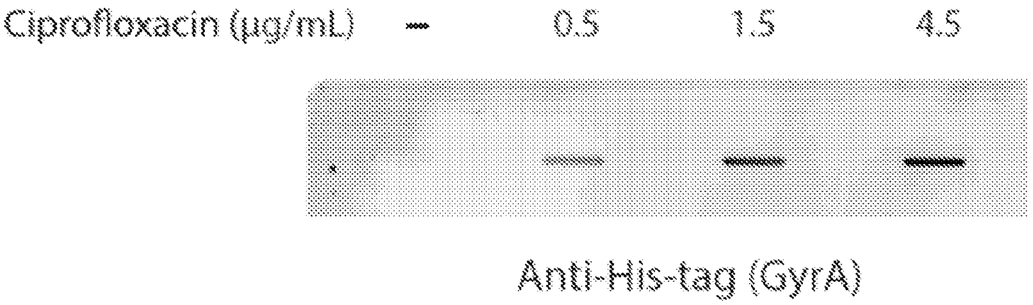
Figure 10A:
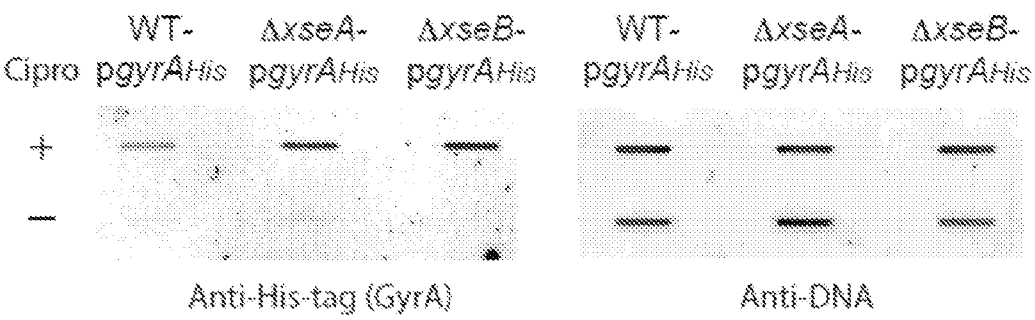
FIG. 10A, FIG. 10B, and FIG. 10C. ExoVII-deficient *E. coli* strains accumulate trapped DNA gyrase upon ciprofloxacin treatment.
Figure 10B:
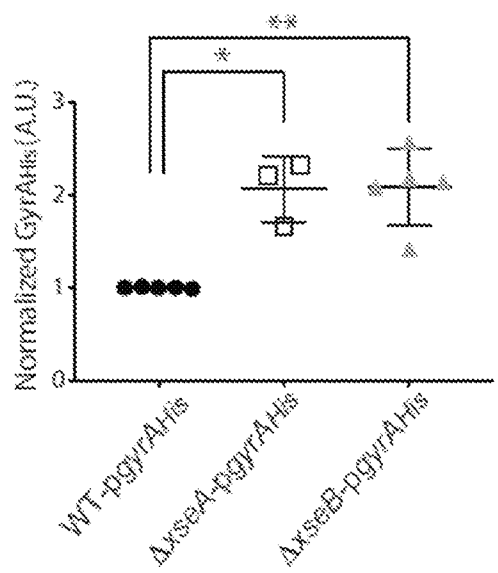
Figure 11A:
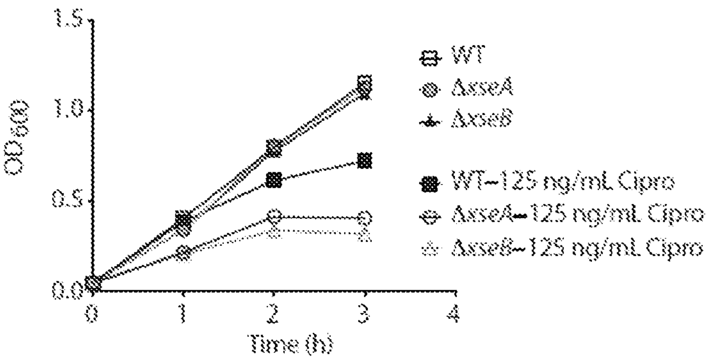
FIG. 11A, FIG. 11B, and FIG. 11C. Loss of ExoVII sensitizes *E. coli* strains to short treatment of ciprofloxacin.
Figure 11B:
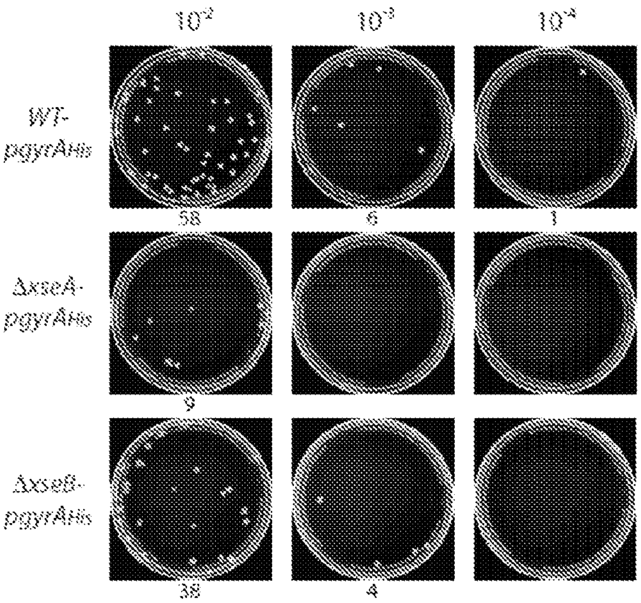
Figure 11C:
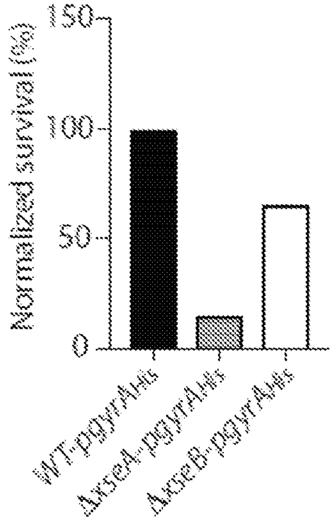

Using these transformant strains, we first optimized a modified rapid approach to DNA adduct recovery (RADAR) assay, which detects endogenously trapped DNA gyrase on genomic DNA (FIG. 9A). Our assay detected trapping of DNA gyrase by ciprofloxacin on genomic DNA in a dose-dependent manner (FIG. 9B). We next compared the amount of trapped DNA gyrase in wild-type vs ExoVII-deficient *E. coli* transformant strains. After 6-hr treatment with ciprofloxacin at 0.5 μg/mL, close to the clinical plasma concentration, ExoVII-deficient transformants (ΔxseA-pgyr$A_{His}$ and ΔxseB-pgyr$A_{His}$) accumulated significantly more trapped DNA gyrase (FIG. 10A-10B). Even with relatively short treatment with ciprofloxacin, ExoVII-deficient strains showed clear hypersensitivity compared to the wild-type strain (FIG. 11). Together these result supports that ExoVII is directly involved in the repair of trapped DNA gyrase.

Figure 10C:
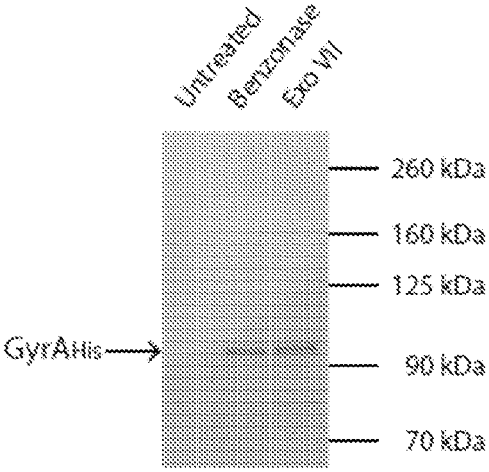

DNA gyrase trapped by ciprofloxacin remains covalently linked to the genomic DNA 5'-ends after the polypeptide chain becomes denatured during DNA purification in the RADAR assay. However, due to the large size of genomic DNA fragments in these enzyme-DNA complexes, they cannot enter polyacrylamide gels unless the DNA is first digested away (FIG. 10C, untreated vs benzonase-treated samples). Treatment of the DNA gyrase covalent complexes with ExoVII released DNA gyrase from the complexes, as detected by immunoblotting of the ExoVII-treated sample (FIG. 10C). This result implies that ExoVII can directly excise trapped endogenous DNA gyrase molecules from DNA after the polypeptides are denatured.

Figure 12A:
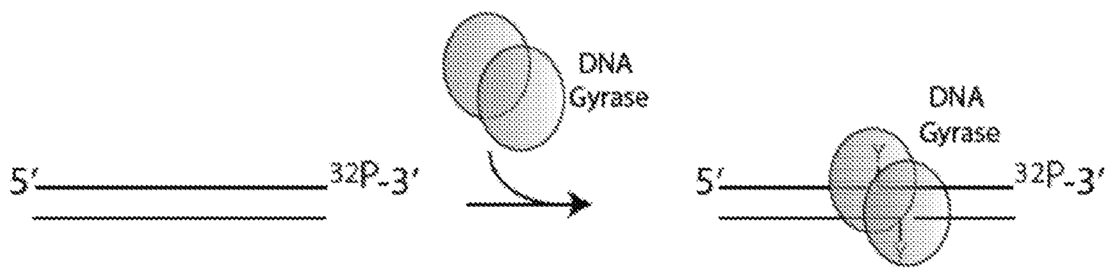
FIG. 12A and FIG. 12B. ExoVII does not resolve intact DNA gyrase covalent complexes.
Figure 12B:
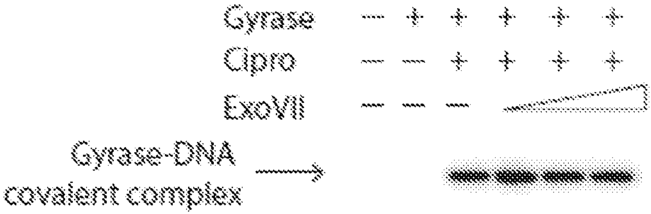
Figure 12B:
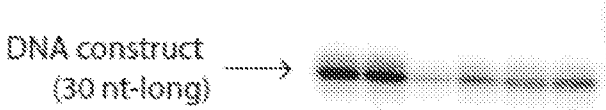

We next asked whether ExoVII can resolve native DNA gyrase covalent complexes. Generated with recombinant DNA gyrase and radio-labeled DNA substrates, DNA gyrase TOPccs were retained in the wells of the sequencing gel and can be distinguished from the free DNA substrates (30-nt long) (FIG. 12). We found that ExoVII failed to resolve the intact DNA gyrase covalent complexes (FIG. 12B). These results indicate that ExoVII is unable to process intact DNA gyrase covalent complexes and likely requires such complexes to undergo digestion or unfolding first, similar to TDP1 and TDP2 in eukaryotes.

Figure 13A:
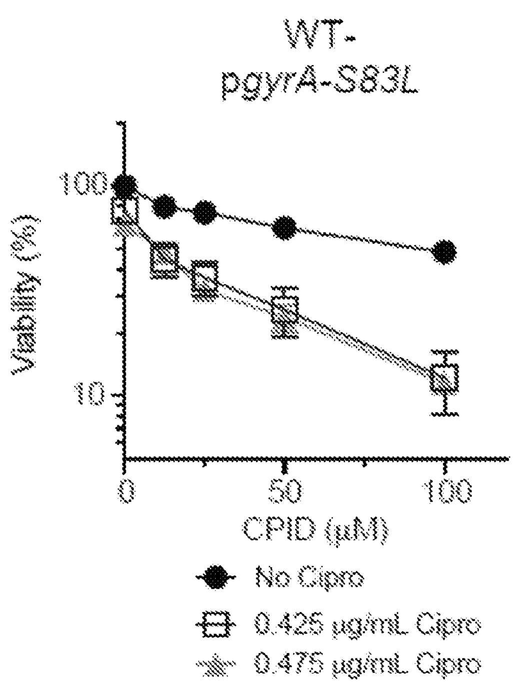
FIG. 13A, FIG. 13B, FIG. 13C, and FIG. 13D. CPID is a specific ExoVII inhibitor.
Figure 13B:
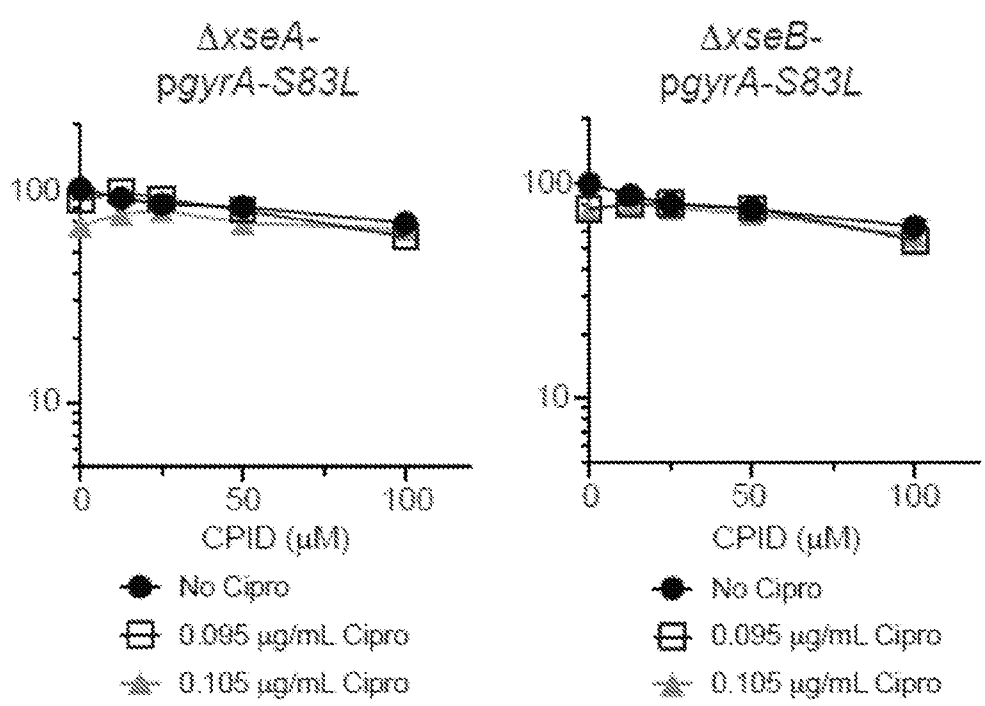
Figure 13C:
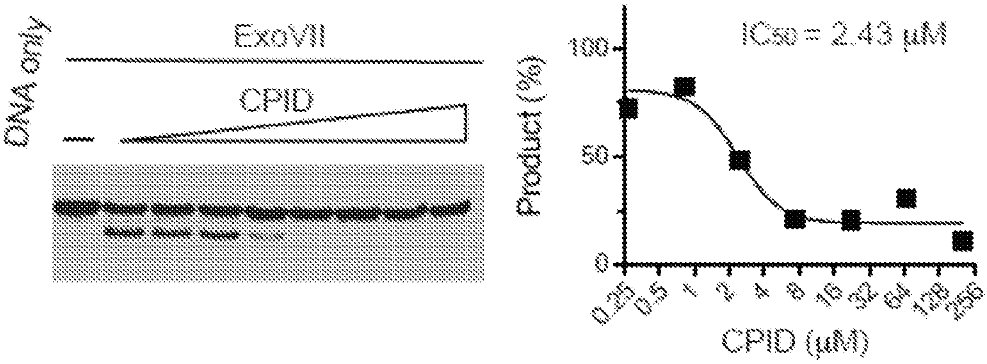
Figure 13D:
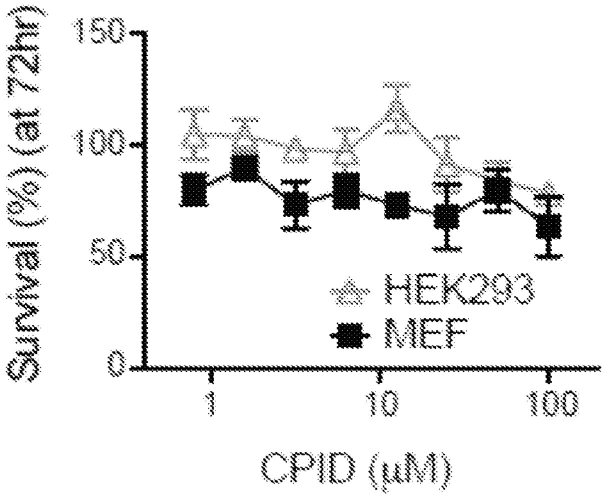

Because genetic inactivation of ExoVII hypersensitizes bacteria to quinolones, we conducted a screen for inhibitors of ExoVII that could synergize with quinolones. Our screen identified a compound from a family of isoquinolinediones that were previously shown to inhibit human TDP2 in vitro but did not synergize with etoposide in cells. The compound 7-(3-chlorophenyl)-1,3(2H,4H)-Isoquinolinedione (CPID) was synergistic with ciprofloxacin in the quinolone-resistant strain (WT-pgyrA-S83L) (FIG. 13A). By contrast, CPID was not synergistic with ciprofloxacin in the strains deficient in either subunit of ExoVII (ΔxseA-pgyrA-S83L or ΔxseB-pgyrA-S83L), suggesting it is a specific inhibitor for ExoVII (FIG. 13B). We next showed that CPID also inhibited ExoVII in vitro with an $IC_{50}$ of 2.43 μM (FIG. 13C). Finally, CPID remained relatively non-toxic to two cell lines, HEK293 and MEF, up to 100 μM after 72-hour treatments (FIG. 13D).

Figure 14:
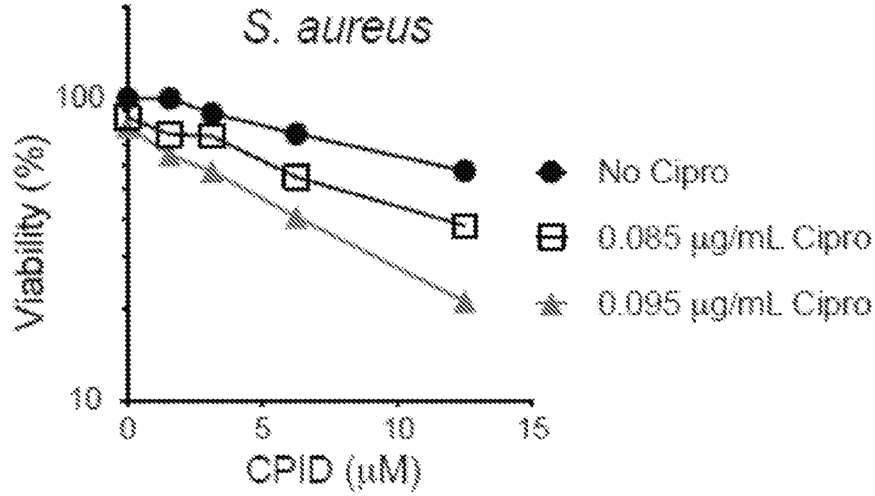
FIG. 14. CPID shows synergistic effect with ciprofloxacin in cultures of *Staphylococcus aureus.*

Since *E. coli* is a gram-negative bacterium, we also tested the synergistic effect of CPID with ciprofloxacin in another important pathogenic gram-positive bacterial species, *Staphylococcus aureus*. We demonstrated clear synergy between CPID and ciprofloxacin in *Staphylococcus aureus* (FIG. 14), establishing the ability of isoquinolinedione compounds to inhibit exonuclease VII across different bacterial species, including gram-positive and gram-negative bacteria.

These experiments show that ExoVII repairs quinolone-induced damage by resolving DNA gyrase covalent complexes. Consistent with the tyrosyl nuclease activity of ExoVII reported here, a recent study employed ExoVII to map trapped Top2 sites in murine cells. The DNA repair function of ExoVII uncovered here provides the missing link accounting for the hypersensitivity of ExoVII-deficient strains to quinolones. It also establishes the presence of a tyrosyl-DNA phosphodiesterase activity in bacteria. The importance of ExoVII is underscored by its conservation across the entire bacteria domain and in some archaea species as well. A recent study showed that, in response to quinolones, XseA is activated by MarA, a transcription factor associated with the multiple antibiotic resistance (mar) operon in *E. coli*, further substantiating the significance of ExoVII in antimicrobial resistance. Our inhibitor screen provides the proof of principle that ExoVII inhibitors act as "helper-drugs" to boost the efficacy of quinolones and to overcome resistance to these antibiotics. Because the substrates of ExoVII and TDP2 share structural similarities (both repair enzymes resolve trapped type IIA topoisomerases), it is plausible that both types of enzymes can be inhibited by the same compound, such as CPID revealed in our study. However, there are clear differences between the two enzymes, as the strongest known TDP2 inhibitor (SV-5-153) failed to inhibit ExoVII.

Generation of *E. coli* Strains

TABLE 1 provides the details of the *E. coli* strains used in this study. All DNA primers used were obtained from IDT with their sequences listed in the accompanying sequence listing. The parental strains (wild type, ΔxseA and ΔxseB) were obtained from the *Coli* Genetic Stock Center at Yale University. The complete gyrA gene including its endogenous promoter and a C-terminal His-tag was cloned from the genomic DNA of *E. coli* K-12 MG1655 strain using gyrAHis FP and BP and introduced into single-copy plasmid pBeloBac11 (NEB) at BamHI and HindIII sites using In-Fusion (TakaRa). The plasmids bearing gyrAHis (pygrHis) were used to transform into the three parental strains using TSS transformation protocol and selected on LB-Cm (10 μg/ml). Transformants were verified with immunoblotting. To generate quinolone-resistant strains, mutation gyrA-S83L was introduced into the same plasmid using QuikChange Lightning (Agilent) and gyrA-S83L FP and BP before establishing transformants. To delete the genomic copy of grA, we first transformed a derivative of wild-type *E. coli* MG1655 carrying the lambda Red-recombineering functions with pgyrAHis, selected on LB-Cm (10 μg/ml) and purified once on the same media at 32° C. A transformant was grown in 10 mL LB-Cm (10 μg/ml) at 32° C. to an $OD_{600}$ of 0.6 and Red function expression was induced for 15 mins at 42° C. Cells were centrifuged and washed four times in ice-cold sterile water and electroporated with 100 ng of a zeoR cassette containing 40-bp homology upstream and downstream of grA generated by PCR reaction with gyrA-KO-zeo-FP and BP. After a 1 hr recovery in 1 mL LB, chromosomal gyrA knock-out clones were selected on LB plates in the presence of Cm (10 μg/ml) and Zeo (25 μg/ml) and incubated at 37° C. overnight. Colonies were purified twice more and the disruption of genomic gyrA was verified by PCR using primers gyrA-KO-FP and BP. A P1 lysate was generated from the knock-out cells and P1 transduction was carried out on cells carrying pBeloBac-gvrA-S83Lhis, as described previously. The disruption of the genomic gyrA in these strains was verified by PCR using primers gyrA-KO-FP and BP. pYtopA and pYtopA-R327W were generated using pBAD/TOPO Thio Fusion Expression Kit (ThermoFisher), and transformants of all three plasmids in the parental strains were obtained using TSS transformation protocol and selected with Amp (100 μg/mL).

TABLE 1

| Strain Name | Genotype |
|---|---|
| WT | BW25113 (Source Yale University CGSC) |
| ΔxseA | BW25113 ΔxseA::Kn |
| ΔxseB | BW25113 ΔxseB::Kn |
| NM1100 | MG1655 mini λ::tet, recombineering Strain |
| NM5000 | NM1100 pBeloBac-gyrAhis recombineered with ΔgyrA::zeo. $Cm^R$ $Zeo^R$ $Tet^S$ |
| WT-pgyrA-S83L | BW25113 pBeloBac-gyrAS83$L_{his}$ transduced with ΔgyrA::zeo from NM50000. $Cm^R$ $Zeo^R$ |
| ΔxseA-pgyrA-S83L | BW25113 DxseA::Kn pBeloBac-gyrAS83Lhis transduced with ΔgyrA::zeo from NM50000. $Cm^R$ $Zeo^R$ |
| ΔxseB-pgyrA-S83L | BW25113 ΔxseB::Kn pBeloBac-gyrAS83Lhis transduced with DgyrA::zeo from NM50000. $Cm^R$ $Zeo^R$ |
| WT-pBAD/Thio | BW25113 pBAD/Thio. $Amp^R$ |
| ΔxseA-pBAD/Thio | BW25113 ΔxseA::Kn pBAD/Thio. $Amp^R$ |
| ΔxseB-pBAD/Thio | BW25113 ΔxseB::Kn pBAD/Thio. $Amp^R$ |
| WT-pYtopA | BW25113 pBAD/Thio-YtopA. $Amp^R$ |
| ΔxseB-pYtopA | BW25113 ΔxseA::Kn pBAD/Thio-YtopA. $Amp^R$ |
| WT-pYtopA-R327W | BW25113 pBAD/Thio-YtopA-R327W. $Amp^R$ |
| ΔxseA-pYtopA-R327W | BW25113 ΔxseA::Kn pBAD/Thio-YtopA-R327W. $Amp^R$ |
| ΔxseB-pYtopA-R327W | BW25113 ΔxseB::Kn pBAD/Thio-YtopA-R327W. $Amp^R$ |
| WT-pgyrAHis | BW25113 pBeloBac-gyrAhis. $Cm^R$ |
| ΔxseA-pgyr$A_{His}$ | BW25113 ΔxseA::Kn pBeloBac-gyr$A_{his}$. $Cm^R$ |
| ΔxseB-pgyr$A_{His}$ | BW25113 ΔxseB::Kn pBeloBac-gyr$A_{his}$. $Cm^R$ |

Spotting and Cell Killing Assays

Exponential growing *E. coli* cultures were diluted to $OD_{600}$ of $10^{-6}$, then 5 μL of 5-fold serial dilution was spotted onto LB plates containing indicated concentration of ciprofloxacin (Cipro) or nalidixic acid (NA) and incubated at 37° C. overnight. For determination of minimum inhibitory concentration (MIC) of ciprofloxacin, 200 μL of exponentially growing culture ($OD_{600}=10^{-1}$) was plated on LB plates, then the MIC Ciprofloxacin test strips (Liofilchem) were applied to the plates and incubated at 37° C. overnight following the manufacturer's instruction. Cell killing assays were carried out as previously described. Briefly, transformants harboring pBAD/Thio, pYtopA or pYtopA-R327W were grown in LB with 2% glucose and 50 μg/mL carbenicillin overnight and diluted 1:100 in LB with 50 μg/mL carbenicillin and grown to $OD_{600}$ of 0.4. YTop1 or YTop1-R327W were induced by addition of 0.2% arabinose for 0.5-2 hrs. Post-induction cultures were then serially diluted and spotted onto LB plates with 2% glucose and 50 μg/mL carbenicillin and incubated at 37° C. overnight. Alternatively, exponentially growing transformants were serially diluted as indicated and spotted on LB plates containing 50 μg/mL carbenicillin and indicated concentrations of arabinose and incubated at 37° C. overnight.

Screen for ExoVII Inhibitor

Exponentially growing WT-pgyrA-S83L, ΔxseA-pgyrA-S83L, or ΔxseA-pgyrA-S83L at $OD_{600}$ of $3\times10^{-4}$ were combined with equal volume of media containing indicated inhibitor concentrations with or without ciprofloxacin at indicated concentrations in clear-bottom 96-well plates. *Staphylococcus aureus* strain HG003 was grown to log phase, then diluted to $OD_{600}$ of $1\times10^{-2}$ before combining with equal volume of media containing indicated concentrations of CPID with or without ciprofloxacin. $OD_{600}$ was measured at the end of 4-hr incubation at 37° C. shaking at 225 rpm and cell densities were normalized to samples without any drug treatment. Toxicity of compounds were measured by treating either HEK293 or MEF (1000 cells in 96-well plates seeded 24-hr prior) with indicated concentrations of ExoVII inhibitor for 72 hours. The samples were imaged with a Cytation 5 (BioTek) and the confluency of each well were normalized to untreated samples.

Generation of DNA Constructs and Biochemical Assays

The biochemical constructs for ExoVII activity were generated as described previously. All oligonucleotides were synthesized by IDT or Midland, and all sequences of DNA oligos are listed in the accompanying sequence listing. For the series of constructs with different chemical groups on 5'-overhangs, a 22-nt DNA with three phosphorothioate bonds on the 3'-ends (T-22-3PT) was labeled with 32P at the 5'-end with [γ-32P]ATP (PerkinElmer Life Sciences) and T4 polynucleotide kinase (NEB), then purified by mini Quick Spin Oligo Columns (Sigma-Aldrich). An 18-nt DNA harboring different chemical groups at the 5'-end (P-18, OH-18 or Y-18) was mixed with the 5'-labeled T-22-3PT before annealing to a complementary strand between 34- and 40-nt long (B-34, B-36, B-38 and B-40) at 1:1:1 ratio. The nicks were sealed with T4 DNA ligase (NEB). For constructs longer than 40 bp, an additional middle piece (M-20 or M40) was also included in the annealing reaction, with the appropriate complementary strands (B56 or B76) before ligation to generate Y-60 and Y-80, each with 4-nt 5'-overhangs. To generate Y-19 with 4-nt 5'-overhangs, Y-18 was labeled on the 3'-end with [α-32P] cordycepin and Terminal Transferase (NEB), then purified by mini Quick Spin Oligo Columns (Sigma-Aldrich) and annealed to B15 at 1:1 ratio. To generate RNA constructs with 5'-phosphotyrosine, T-22-3PT was labeled with $^{32}P$ at the 5'-end as described before, mixed with Y-10-DNA or Y-10-RNA, before annealing to B28 or B32 at 1:1:1 ratio in the presence of 3 U/μL of RNasin® Plus (Promega). For the series of constructs with different chemical groups on 3'-overhangs, a 14-nt DNA harboring different chemical groups at the 3'-end (14-P, 14-OH or 14-Y) was labeled with $^{32}P$ at the 5'-end as described before, then mixed with T22 and annealed to B32-3Y or B36-3Y at 1:1:1 ratio, followed by DNA ligation. For single-stranded constructs, T22-15PT (15 phosphorothioate bonds on the 3'-ends) was labeled with 32P at the 5'-end as described before, then mixed with OH-18 or Y-18 at 1:1 ratio and ligated with T4 RNA Ligase 1 (NEB) following the manufacturer's instructions. For generation of *E. coli* DNA gyrase covalent complexes, Gyr-1 was labeled on the 3'-end with [α-$^{32}$P] cordycepin and Terminal Transferase (NEB), then purified by mini Quick Spin Oligo Columns (Sigma-Aldrich) and annealed to Gyr-2 at 1:1 ratio.

Reactions with ExoVII (ThermoFisher or NEB) were performed in 10 μL reaction containing 20-100 nM internally ratio-labeled DNA substrate and indicated concentration of ExoVII in buffer with 50 mM potassium acetate, 20 mM tris-acetate (pH=7.9), 10 mM magnesium acetate and 1 mM DTT. ExoVII reactions were incubated at 37° C. for 1 or 2 hrs followed by inactivation at 55° C. for 30 mins before terminated by addition of 20 μL formamide gel loading buffer (96% (v/v) formamide, 10 mM ethylenediaminetetraacetic acid, 1% (w/v) xylene cyanol and 1% (w/v) bromophenol blue). For IC50 determination, ExoVII was preincubated with the inhibitor at 25° C. for 5 mins before addition of equal volume of DNA solution and the reaction continued for another 20-30 mins. The 10 μL reaction contained 0.025 U/μL ExoVII, 20-100 nM internally ratio-labeled DNA substrate, and indicated inhibitor concentration in buffer with 50 mM potassium acetate, 20 mM trisacetate (pH=7.9), 10 mM magnesium acetate, 1 mM DTT and 10% (v/v) DMSO. The percentage of products in the presence of inhibitor was normalized to that of control reaction without any inhibitors, and resulting plot was fitted to a nonlinear regression function in Prism. DNA gyrase was purified as previously described. Reactions with DNA gyrase were performed in 10 μL reaction containing 20-100 nM radio-labeled DNA substrate, 40 nM DNA gyrase and 250 nM ciprofloxacin when indicated.

Reaction buffer contains 35 mM Tris-HCl (pH=7.5), 24 mM KCl, 4 mM $MgCl_2$, 2 mM DTT, 1.7 mM spermidine, 0.36 mg/mL BSA, 1 mM ATP, and 6.5% glycerol. After incubation at 25° C. for 1 hr, 0.375 to 1.5 U/μL of ExoVII were added and the reactions were incubated further at 37° C. for 3 hrs. The reactions were stopped with 0.2% SDS and 20 μL formamide gel loading buffer (96% (v/v) formamide, 10 mM ethylenediaminetetraacetic acid, 1% (w/v) xylene cyanol and 1% (w/v) bromophenol blue). All samples were heat denatured at 95° C. for 5 mins and analyzed by denaturing PAGE (20%). Gels were dried and exposed on PhosphorImager screens. Imaging was done using a Typhoon 8600 imager (GE Healthcare, Little Chalfont, United Kingdom).

Rapid Approach to DNA Recovery (Radar) Assays

Exponentially growing *E. coli* cells ($OD_{600}$=0.4) were treated with 0.5 μg/mL ciprofloxacin for 6 hrs, then 1 mL of treated cells was directly combined with 4 mL of 1.25× lysis buffer (7.5 M guanidinium isothiocyanate, 12.5 mM Tris-HCl (pH=6.5), 25 mM EDTA, 5% Triton X-100, and 1.25% lauroylsarcosine). The lysates were sonicated for 3 cycles, each for 15 secs at 60% power, then were phenol-chloroform extracted twice. The samples were ethanol precipitated and the DNA pellets washed twice with 80% ethanol before being air dried. The DNA pellets were resuspended in 8 mM NaOH and DNA concentrations of samples were quantified. Equal amount of DNA (8 μg) of each sample was blotted on PVDF membrane and probed with anti-His-tag rabbit monoclonal antibody (Cell Signaling) and anti-ds DNA mouse monoclonal antibody (Abcam), and the band intensities were quantified by ChemiDoc System (Bio-Rad). Alternatively, 5 μg of purified DNA from ciprofloxacin-treated samples was treated with 25 U/μL benzonase (Millipore Sigma) or 1 U/μL ExoVII at 37° C. for 2 hrs in a buffer containing 50 mM potassium acetate, 20 mM tris-acetate (pH=7.9), 10 mM magnesium acetate and 1 mM DTT. The samples were then resolved on a 6% Tris-Glycine gel and immunoblotting was done following standard procedures and probed with anti-His-tag rabbit monoclonal antibody (Cell Signaling).

Sequences

Sequences used are provided in TABLE 2.

TABLE 2

| SEQ ID NO | Name | Sequence | Modification |
|---|---|---|---|
| 1 | gyrA$_{His}$ FP | 5'-CGGTACCCGGGGATCCGGATGTGAAT AAAGCGTATAGG | |
| 2 | gyrA$_{His}$ BP | 5'-TAGAATACTCAAGCTTTTAGTGGTGAT GGTGATGATGTTCTTCTTCTGGCTCGTC GTCAACG | |
| 3 | gyrA-S83L FP | 5'-CATGGTGACTTGGCGGTCTAT | |
| 4 | gyrA-S83L BP | 5'-ATAGACCGCCAAGTCACCATG | |
| 5 | gyrA-KO-zeo-FP | 5'-TACTCCGTAATTGGCAAGACAAACGA GTATATCAGGCATTGTTGACAATTAAT CATCGGC | |
| 6 | gyrA-KO-zeo-BP | 5'-AAGGGAGATAGCTCCCTTTTGGCATGA AGAAGTAAAATTATCAGTCCTGCTCCT CGGCCA | |
| 7 | gyrA-KO-FP | 5'-TCATTGGCACTTCTACTCCG | |
| 8 | gyrA-KO-BP | 5'-AAGGGAGATAGCTCCCTTTT | |
| 9 | T-22-3PT | 5'-GCGCAGCTAGCGGCGGATG*G*C*A | * = phosphorothioate bond |
| 10 | P-18 | 5'-P-TCCGTTGAAGCCTGCTTT | P = phosphate |
| 11 | OH-18 | 5'-TCCGTTGAAGCCTGCTTT | |
| 12 | Y-18 | 5'-Y-TCCGTTGAAGCCTGCTTT | Y = phosphotyrosine |
| 13 | OH-19 | 5'-TTCCGTTGAAGCCTGCTTT | |
| 14 | B-34 | 5'-TGCCATCCGCCGCTAGCTGCGCAAAGC AGGCTTC | |
| 15 | B-36 | 5'-TGCCATCCGCCGCTAGCTGCGCAAAGC AGGCTTCAA | |
| 16 | B-38 | 5'-TGCCATCCGCCGCTAGCTGCGCAAAGC AGGCTTCAACG | |
| 17 | B-40 | 5'-TGCCATCCGCCGCTAGCTGCGCAAAGC AGGCTTCAACGGA | |
| 18 | B-15 | 5'-TAAAGCAGGCTTCAA | |
| 19 | B-56 | 5'-TGCCATCCGCCGCTAGCTGCGCACTCT TGACCCTACGACGATAAAGCAGGCTTCAA | |
| 20 | B-76 | 5'-TGCCATCCGCCGCTAGCTGCGCACTCT TGACCCTACGACGATACTCTTGACCCT ACGACGATAAAGCAGGCTTCAA | |
| 21 | M-20 | 5'-P-ATCGTCGTAGGGTCAAGAGT | P = phosphate |
| 22 | M-40 | 5'-P-ATCGTCGTAGGGTCAAGAGTATCGTCG TAGGGTCAAGAGT | P = phosphate |
| 23 | Y-10-DNA | 5'-Y-TTAAAACAGC | Y = phosphotyrosine |

TABLE 2-continued

| SEQ ID NO | Name | Sequence | Modification |
|---|---|---|---|
| 24 | Y-10-RNA | 5'Y-rUrUrArArArArCrArGrC | Y = phosphotyrosine |
| 25 | B-28 | 5'-TGCCATCCGCCGCTAGCTGCGCGCTGTT | |
| 26 | B-32 | 5'-TGCCATCCGCCGCTAGCTGCGCGCTGT TTTAA | |
| 27 | T-22 | 5'-GCGCAGCTAGCGGCGGATGGCA | |
| 28 | 14-P | 5'-GATCTAAAAGACTT-P | P = phosphate |
| 29 | 14-OH | 5'-GATCTAAAAGACTT | |
| 30 | 14-Y | 5'-GATCTAAAAGACTT-Y | Y = phosphotyrosine |
| 31 | B32-3Y | 5'-CTTTTAGATCTGCCATCCGCCGCTAGC TGCGC | |
| 32 | B36-3Y | 5'-AAGTCTTTTAGATCTGCCATCCGCCGC TAGCTGCGC | |
| 33 | T-22-15PT | 5'-GCGCAGC*T*A*G*C*G*G*C*G*G*A*T* G*G*C*A | * = phosphorothioate bond |
| 34 | Gyr-1 | 5'-GAATCATAATGGGGAAGGCCATCCAGCCTC | |
| 35 | Gyr-2 | 5'-TGAGGCTGGATGGCCTTCCCCATTATG ATTC | |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

The invention claimed is:

1. A method of treating a bacterial infection in a subject comprising administering a therapeutically effective amount of a combination of a bacterial type IIA topoisomerase inhibitor, or a pharmaceutically acceptable salt thereof and a compound Formula I, or a pharmaceutically acceptable salt thereof, to the subject, where the compound of Formula I is (Formula (I))

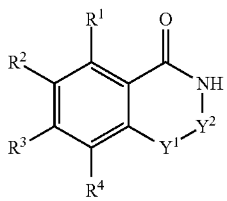

$Y^1$ is carbon substituted with oxo and $Y^2$ is $CR^6$; or $Y^1$ is $CR^5$ and $Y^2$ is carbon substituted with oxo;

$R^1$, $R^3$, and $R^4$ are independently chosen from H, halogen, hydroxyl, amino, nitro, cyano, $C_1$-$C_4$alkyl, $C_1$-$C_4$alkoxy, $C_1$-$C_2$haloalkyl, and $C_1$-$C_2$haloalkoxy;

$R^2$ is H, halogen, hydroxyl, amino, nitro, cyano, —COOH, $C_1$-$C_4$alkyl, $C_1$-$C_4$alkoxy, $C_1$-$C_2$haloalkyl, or $C_1$-$C_2$haloalkoxy; or $R^2$ is —$C_0$-$C_2$alkyl ($C_3$-$C_2$cycloalkyl), —$C_0$-$C_2$alkyl (aryl), —$C_0$-$C_2$alkyl (pyridyl), or —$C_0$-$C_2$alkyl (furanyl), each of which is optionally substituted with one or more substituents independently chosen from $R^{10}$, $R^4$ is H, halogen, hydroxyl, amino, nitro, cyano, $C_1$-$C_4$alkyl, $C_1$-$C_4$alkoxy, $C_2$-$C_6$alkanoyl, —$C_1$-$C_6$alkylester, —$C_0$-$C_4$alkyl (mono- or di-$C_1$-$C_6$alkylamino), mono- or di-$C_1$-$C_6$alkylcarboxamide; $C_1$-$C_2$haloalkyl, or $C_1$-$C_2$haloalkoxy;

$R^5$ and $R^6$ are independently chosen from H, halogen, hydroxyl, amino, nitro, cyano, —CHO, —COOH, —$CONH_3$, $C_1$-$C_4$alkyl, $C_1$-$C_4$alkoxy, $C_1$-$C_2$haloalkyl, $C_1$-$C_2$haloalkoxy, $C_2$-$C_6$alkanoyl, $C_1$-$C_6$alkylester, —$C_0$-$C_4$alkyl (mono- and di-$C_1$-$C_6$alkylamino), and mono- and di-($C_1$-$C_6$alkyl) carboxamide;

$R^{10}$ is independently selected at each occurrence from halogen, hydroxyl, amino, nitro, cyano, —CHO, —COOH, oxo, $C_1$-$C_8$alkyl, $C_2$-$C_8$alkenyl, and $C_2$-$C_8$alkynyl, wherein in each $C_1$-$C_8$alkyl, $C_2$-$C_8$alkenyl, and $C_2$-$C_8$alkynyl, in the definition of $R^{10}$ one or more carbon atoms is optionally replaced by O, $NR^{11}$, —C(O)—, —$NR^{11}$C(O)—, —C(O)$NR^{11}$—, —C(O)O—, —OC(O)—, —$S(O)_n$—, —$S(O)_nNR^{11}$—, or —$NR^{11}S(O)_n$—, where n is 0, 1, or 2, and in which each $C_0$-$C_4$alkyl, $C_1$-$C_8$alkyl, $C_2$-$C_8$alkenyl, or $C_2$-$C_8$alkynyl is optionally substituted with one or more substituents $R^{13}$;

$R^{11}$ is independently chosen at each occurrence from hydrogen, $C_1$-$C_6$alkyl, and —$C_0$-$C_2$alkyl ($C_3$-$C_2$cycloalkyl); and $R^{13}$ is independently chosen at each occurrence from halogen, hydroxyl, amino, nitro, cyano, —CHO, —COOH, oxo, $C_3$-$C_7$cycloalkyl, and phenyl.

2. The method of claim 1, wherein the type IIA topoisomerase inhibitor is a quinolone antibiotic or a pharmaceutically acceptable salt thereof.

3. The method of claim 2, wherein the quinolone antibiotic is cinoxacin, ciprofloxacin, delafloxacin, gatifloxacin, gemifloxacin, lomefloxacin, moxiflaxacin, nalidixic acid, norfloxacin, ofloxacin, sparfloxacin, or trovafloxacin.

4. The method of claim 1, wherein the compound of Formula I is a compound or pharmaceutically acceptable salt of Formula I-A (Formula I-A)

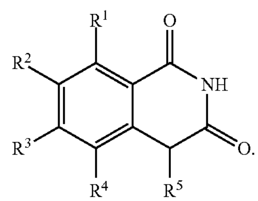

5. The method of claim 4, wherein $R^1$, $R^3$, $R^4$, and $R^5$ are each independently chosen from H and methyl; and $R^2$ is phenyl, furanyl, or pyridyl each of which is optionally substituted with one or more substituents independently chosen from $R^{10}$.

6. The method of claim 4, wherein $R^1$, $R^2$, and $R^4$ are independently chosen from H and methyl;

$R^3$ is H, halogen, hydroxyl, or nitro; and $R^5$ is H or $C_1$-$C_6$alkylester; where one of $R^3$ and $R^5$ is other than H.

7. The method of claim 1, wherein the compound is a compound or pharmaceutically acceptable salt of Formula I-B (Formula I-B)

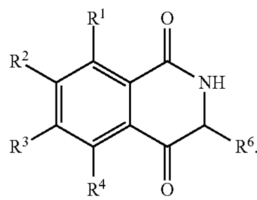

8. The method of claim 7, wherein $R^1$, $R^2$, $R^3$, and $R^4$ are independently chosen from H and methyl; and $R^6$ is —$CONH_3$, —COOH, $C_1$-$C_6$alkyl ester, or $C_1$-$C_6$alkylcarboxaminde.

9. The method of claim 1, wherein the compound is a compound of any of the following structures, or a pharmaceutically acceptable salt thereof

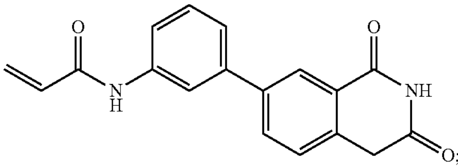

;

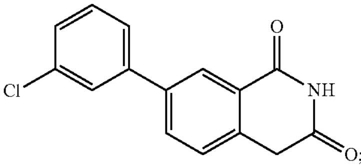

;

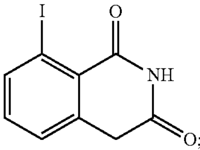

;

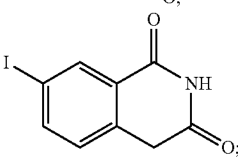

;

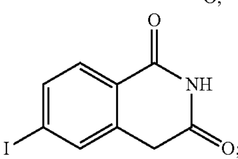

;

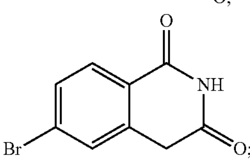

;

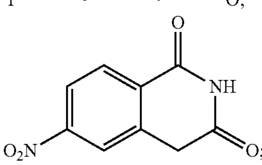

;

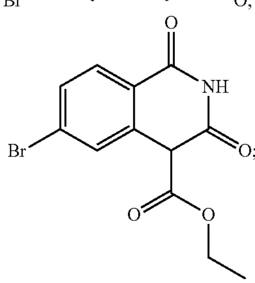

;

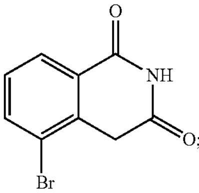

;

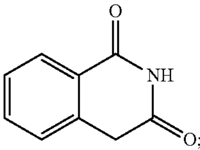

; and

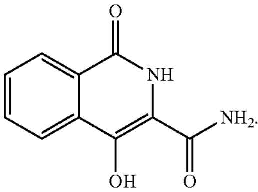

.

10. The method of claim 1 wherein the therapeutically effective amount of the quinolone antibiotic and the compound of Formula I or pharmaceutically acceptable salt thereof are administered to the subject as a pharmaceutical dosage form comprising the quinolone antibiotic and the compound or pharmaceutically acceptable salt of Formula I.

11. The method of claim 1, wherein the subject has a Gram negative bacterial infection.

12. The method of claim 1, wherein the subject has a Gram positive bacterial infection.

13. The method of claim 1, wherein the bacterial infection comprises *E. coli* or *Staphylococcus aureus*.

14. The method of claim 2 wherein the compound of Formula I is a compound or pharmaceutically acceptable salt of Formula I-A (Formula I-A)

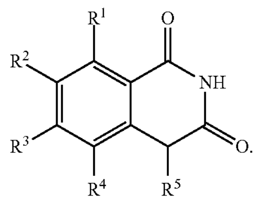

15. The method of claim 14, wherein $R^1$, $R^3$, $R^4$, and $R^5$ are each independently chosen from H and methyl; and $R^2$ is phenyl, furanyl, or pyridyl each of which is optionally substituted with one or more substituents independently chosen from $R^{10}$.

16. The method of claim 14, wherein $R^1$, $R^2$, and $R^4$ are independently chosen from H and methyl;

$R^3$ is H, halogen, hydroxyl, or nitro; and $R^5$ is H or $C_1$-$C_6$alkylester; where one of $R^3$ and $R^5$ is other than H.

17. The method of claim 2 wherein the compound is a compound or pharmaceutically acceptable salt of Formula I-B (Formula I-B)

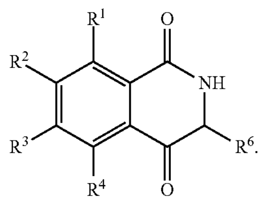

18. The method of claim 17, wherein $R^1$, $R^2$, $R^3$, and $R^4$ are independently chosen from H and methyl; and $R^6$ is —$CONH_3$, —COOH, $C_1$-$C_6$alkyl ester, or $C_1$-$C_6$alkylcarboxaminde.

19. The method of claim 3 wherein the compound of Formula I is a compound or pharmaceutically acceptable salt of Formula I-A (Formula I-A)

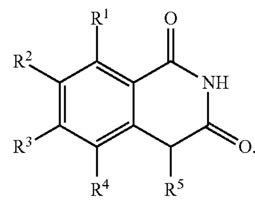

20. The method of claim 3 wherein the compound is a compound or pharmaceutically acceptable salt of Formula I-B (Formula I-B)

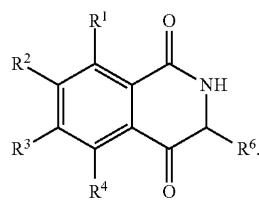

21. The method of claim 1 wherein the type IIA topoisomerase inhibitor is ciprofloxacin and wherein the compound of Formula I is

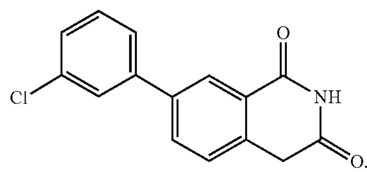 [SMILES: O=C1Cc2ccc(-c3cccc(Cl)c3)cc2C(=O)N1]

* * * * *